(12) United States Patent
Wang et al.

(10) Patent No.: US 7,932,391 B2
(45) Date of Patent: Apr. 26, 2011

(54) METHOD FOR THE PREPARATION OF CLOPIDOGREL AND ITS ANALOGUES OF METHYL-TETRAHYDROTHIENO[3,2-C]PYRIDINE ACETATE

(75) Inventors: Lixin Wang, Sichuan (CN); Yi Tang, Sichuan (CN); Yi Chen, Sichuan (CN); Fang Tian, Sichuan (CN)

(73) Assignees: Zhejiang Hauhai Pharmaceutical Co., Ltd., Zhejiang (CN); Chengdu Organic Chemicals Co., Ltd., Chinese Academy of Sciences, Sichuan (CN)

( * ) Notice: Subject to any disclaimer, the term of this patent is extended or adjusted under 35 U.S.C. 154(b) by 445 days.

(21) Appl. No.: 12/066,187

(22) PCT Filed: Sep. 7, 2006

(86) PCT No.: PCT/CN2006/002316
§ 371 (c)(1),
(2), (4) Date: Apr. 11, 2008

(87) PCT Pub. No.: WO2007/028337
PCT Pub. Date: Mar. 15, 2007

(65) Prior Publication Data
US 2008/0249311 A1  Oct. 9, 2008

(30) Foreign Application Priority Data

Sep. 8, 2005  (CN) .......................... 2005 1 0060719
Sep. 8, 2005  (CN) .......................... 2005 1 0060720
Sep. 8, 2005  (CN) .......................... 2005 1 0060721
Sep. 8, 2005  (CN) .......................... 2005 1 0060722
Oct. 21, 2005 (CN) .......................... 2005 1 0061230
Oct. 21, 2005 (CN) .......................... 2005 1 0061231

(51) Int. Cl.
*C07D 513/02* (2006.01)
(52) U.S. Cl. ..................................................... 546/114
(58) Field of Classification Search .................... 546/114
See application file for complete search history.

(56) References Cited

U.S. PATENT DOCUMENTS
5,204,469 A   4/1993  Descamps et al.

FOREIGN PATENT DOCUMENTS
CN        1487943 A     4/2004
(Continued)

OTHER PUBLICATIONS
Burgess et al. Tetrahedron Letters. 1997 38 1681-1684.*
(Continued)

*Primary Examiner* — Nizal S Chandrakumar
(74) *Attorney, Agent, or Firm* — Panitch Schwarze Belisario & Nadel LLP

(57) ABSTRACT

The present invention disclosed a preparation method of Clopidogrel (X=2-Cl) and its analogues of methyl tetrahydrothienopyridine acetate (I) by using halogen phenyl acetonitrile (VIII) as starting material and tetrahydrothienopyridine acetonitrile (IV), tetrahydrothienopyridine acetate (V) as key intermediates, and further using kinetic resolution to prepare the optical active Clopidogrel and compounds of methyl tetrahydrothenopridine acetate of formula (XII). The Clopidogrel of present invention is a novel high effective and safety drug for inhibition of platelet aggregation. This invention applied systematic technique of racemization of unwanted optical active enantiomer, recover recycle and reuse of resolution agent etc., with greater economic advantages and suitable for commercial scale industrial production.

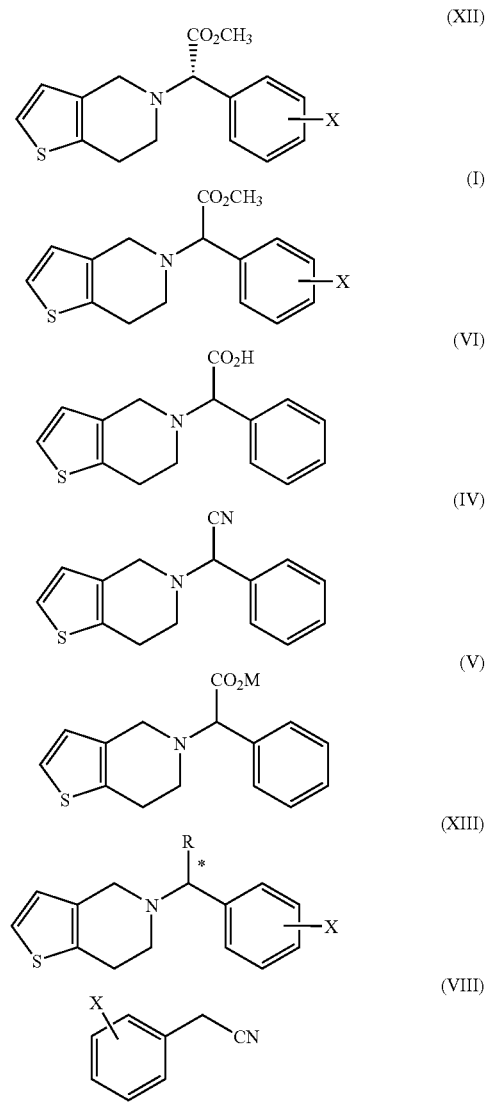

Wherein: X represents atoms of hydrogen, fluorine, chlorine, bromine or iodine, M represents an alkali metal ion.

34 Claims, No Drawings

FOREIGN PATENT DOCUMENTS

| EP | 0420706 | A2 | 4/1991 |
| WO | 02059128 | A2 | 8/2002 |
| WO | 03035652 | A1 | 5/2003 |
| WO | 2005026174 | A1 | 3/2005 |

OTHER PUBLICATIONS

International Search Report and Written Opinion dated Dec. 28, 2006 in International Application No. PCT/CN2006/002316.

Alain Burgos et al., "ortho-Metalation/Chlorination of Benzoic Acid Derivatives: Preparation of [benzene-U-13C]-rac-Clopidogrel([benzene-U-13C]-rac-SR25990C"J. Labelled Cpd. Radiopharm., 2000, vol. 43, pp. 891-898.

Supplementary European Search Report dated Jul. 5, 2010 in European Application No. 06775625.4.

* cited by examiner

METHOD FOR THE PREPARATION OF CLOPIDOGREL AND ITS ANALOGUES OF METHYL-TETRAHYDROTHIENO[3,2-C]PYRIDINE ACETATE

CROSS-REFERENCE TO RELATED APPLICATION

This application is a section 371 of International Application No. PCT/CN2006/002316, filed Sep. 7, 2006, which was published in the Chinese language on Mar. 15, 2007, under International Publication No. WO 2007/028337 A1 and the disclosure of which is incorporated herein by reference.

FIELD OF THE INVENTION

The present invention relates to the preparation of chiral compounds and particularly relates to a systematic method for the preparation of Clopidogrel as a representative compound and of its methyl tetrahydrothienopyridine acetate analogues, their kinetic resolution, the racemization of unwanted chiral compounds and their comprehensive utilization, and also the recovery of chiral resolution agents and their recycled utilization.

BACKGROUND OF THE INVENTION

Cardiac and cerebral thrombosis are common diseases, of which coronary thrombosis and cerebral thrombosis, as the main thrombosis diseases, are taking place increasingly in recent years and greatly affecting people's health. The preventive and therapeutic researches of these diseases are very important. Platelet aggregation is a key step in normal blood agglutination mechanism. Both platelet adhesion and aggregation are the major initial steps in thromogenesis. Therefore, pharmaceuticals for the inhibition of platelet aggregation play a very important role in the treatment of thrombotic diseases, and the invention of anti-thrombosis drugs is always a hot topic in the research of such fields.

Clopiodogrel is a novel high effective and safety anti-thrombosis drug with the structure of (S)-(+)-Clopidogrel bisulfate (XII, wherein: X=2-Cl). Which was first of all disclosed in FR 2215948, FR 2530247 and FR 2612929 by French Sanofi Co., and was invented successfully in 1986. Clinically this drug is used in the treatment of atherosclerosis, acute coronary syndrome (ACS) and thrombosis complication. Clopidogrel was first marketed in United States on March 1998, and later was entered into markets of Europe, Canada, Australia and Singapore etc., and the demands are increased gradually in worldwide.

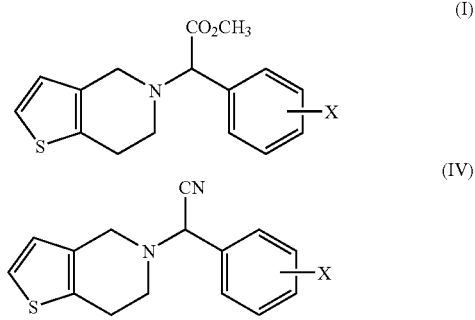

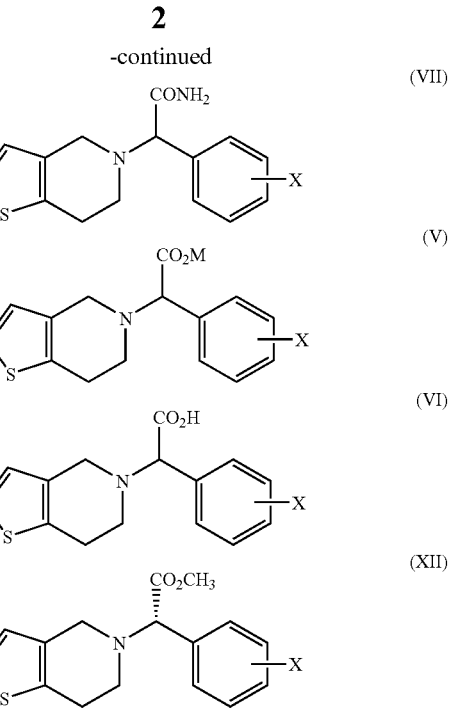

Formula (I) is the racemic compound of Clopidogrel and its analogue methyl tetrahydrothieno[3,2-c]pyridine acetate As reported, the present methods (U.S. Pat. No. 4,529,596, GB 0420706, GB 0466569, U.S. Pat. No. 5,204,469, EP 465358, EP99802, EP 420706) to obtain Clopiodogrel and compound of formula (XII) is generally performed by using α-halogen phenylacetic acid derivatives as starting raw material to react and derivatize with thiophenylethylamine. In the mentioned methods, compound of formula (IV) and its analog acetonitrile derivatives (WO9851689, WO9851681) could not be hydrolyzed directly to obtain compound of formula (V) or compound of formula (VI). All of them are indirectly hydrolyzed into tetrahydrothienopyridine acetamide derivatives of formula (VII) and further hydrolyzed to obtain compound of formula (I) (WO02059128, CN1487943A).

Recently, Cadila Heath Care LTD of India reported a method for the preparation of compound in formula (IV) (WO02059128, CN 1487943A), in which the compound of formula (IV) could be used to prepare compound of formula (VII) effectively in suitable conditions, and then derivatized to prepare compound of formula (V), compound of formula (VI) and compound of formula (I). In their preparation example, however, did not provide example of alkaline hydrolysis. In fact, we had carried out the preparation according to the method and conditions those they provided, but only could obtain compound of formula (VII), or though we can obtain compound of formula (V) and compound of formula (VI) but with no separation and manufacturing values due to too low yield. In the mean time, the acid hydrolysis method and conditions that patent provided also have no competitive ability due to too low yield (only 38%).

The preparation of the target products and related intermediates can also refer to following references and patents: Journal of Chinese Pharmaceutical Industry 2002, 33 (4) 206, WO9851681, WO9851682, WO9851689, WO9918110, U.S. Pat. No. 4,876,362, U.S. Pat. No. 5,036,156, U.S. Pat. No. 5,132,435, U.S. Pat. No. 5,139,170, U.S. Pat. No. 5,204,469 and U.S. Pat. No. 6,080,875 etc.

Clopidogrel possesses one asymmetric carbon with two chiral isomers, i.e., a (S)-Clopidogrel and a (R)-Clopidogrel. Only (S)-Clopidogrel and its salts possess physiological activities.

(S)-Clopidogrel and the needed chiral intermediates can be obtained from the above mentioned chiral compound synthetic methods or resolution of racemic Clopidogrel and correspondent intermediates (U.S. Pat. No. 6,737,411B2, WO2004074215, U.S. Pat. No. 4,847,265, U.S. Pat. No. 6,215,005B1, U.S. Pat. No. 6,258,961B1).

U.S. Pat. No. 6,737,411B2 reported a process for the synthesize salts of (S)-Clopidogrel by reacting a mixture of (S)- and (R)-Clopidogrel free base with 0.6-0.8 molar of levorotatory camphor sulfonic acid to form camphor sulfonate in a solvent of a $C_5$-$C_{12}$ hydrocarbon such as benzene, toluene, xylene, chlorobenzene and a solvent mixture of DMF, butanol or acetone etc. to perform resolution by crystallization, and then synthesize the (S)-Clopidogrel and its salts.

WO2004074215 reported a process for preparation of (S)-Clopidogrel and its salts while using more concentrated than 1 molar levorotatory camphor sulfonic acid in large amount of isopropanol to prepare low yielding (<50%) (S)-Clopidogrel camphor sulfonate by resolution with crystallization and then synthesize the (S)-Clopidogrel and its salts.

U.S. Pat. No. 4,847,265 reported a process to obtain target chiral isomers by levorotatory camphor sulfonic acid in solvents such as DMF, ketones and alcohols etc. from resolution of compounds in the form of (S)-Clopidogrel levorotatory camphor sulfonate.

In earlier patents such as U.S. Pat. No. 5,132,435, U.S. Pat. No. 6,215,005, U.S. Pat. No. 6,258,961 and their cited patents and literatures, almost all the chiral resolution strategies were based on the different solubilities between (S)-Clopidogrel camphor sulfonate and (R)-Clopidogrel camphor sulfonate in acetone.

Summarily, the present reported methods or processes for chiral resolution to separate the racemic Clopidogrel are almost all based on the different solubilities between (S)-Clopidogrel camphor sulfonate and (R)-Clopidogrel camphor sulfonate in acetone, DMF, alcohol or their mixtures with other solvents with less solubilities by means of many times of classical recrystallization to reach effective resolution.

For economical and large scale synthesize the target chiral compounds and, in the same time, for solving problems of eliminate (storage) the "wastes" in the way of environmental protection, it is necessary to solve problems of racemization, recovery and utilization of the unwanted chiral compounds or intermediates, the recovery and recycle of the chiral resolving agents. WO 02/059128A2 etc. reported the racemization and recycle of the unwanted chiral (R)-Clopidogrel intermediate (VII), while they did not offer the details of racemization. US2004/0024012A1 disclosed the racemization of (R)-Clopidogrel with strong base (such as potassium t-butoxide), while the yield and ee value were not offered in the examples. US2005/0059696A1 reported a process of refluxing and racemization of unwanted chiral (R)-Clopidogrel in NaOH solution to obtain compounds (V) to realize the recovery and utilization.

In all the reported methods, several of following problems are still to be solved: (1) How to manufacture Clopidogrel and its methyl tetrahydrothienopyridine acetate analogues in an economical, effective, environmental protective, commercialize and industrialize way; (2) resolution efficiency; (3) the consumption amount and recycle or reuse of the chiral resolution agents such as camphor sulfonic acid and tartaric acid etc.; (4) selection and optimization of solvents and their consumption; (5) reliability and cost efficiency of resolution method used.

SUMMARY OF THE INVENTION

The objects of the present invention are to overcome the drawbacks of the above reported processes and to devise a novel synthetic route and an effective process for the preparation of (S)-(+)-Clopidogrel, its methyl tetrahydrothienopyridine acetate analogues.

The present invention firstly discloses a novel, efficient and economical synthetic route and process for the preparation of racemic methyl tetrahydrothienopyridine acetate compounds (I) represented by racemic Clopidogrel.

The present invention also provides a novel, efficient and economical method for kinetic resolution of racemic Clopidogrel in the way of industrialize and commercialize scale and with production and environmental protective superiorities.

The invention also provides a new method for recovery and utilization of chiral resolution agents and an economical and commercial method facilitate to industrialize production of tetrahydrothienopyridine biological optical isomer derivatives and racemization, recovery and recycled utilization.

DETAILED DESCRIPTIONS OF THE INVENTION

The technique scheme, synthetic route and the processes for the preparations, chiral resolution, racemization and reuse of the chiral resolving agent mentioned in the above or anywhere in this patent are outlined in the following schemes (only as illustrations and should not be construed as limitations to the scope of the invention).

Scheme 1 Preparations of Clopidogrel, its derviatives and related intermediates

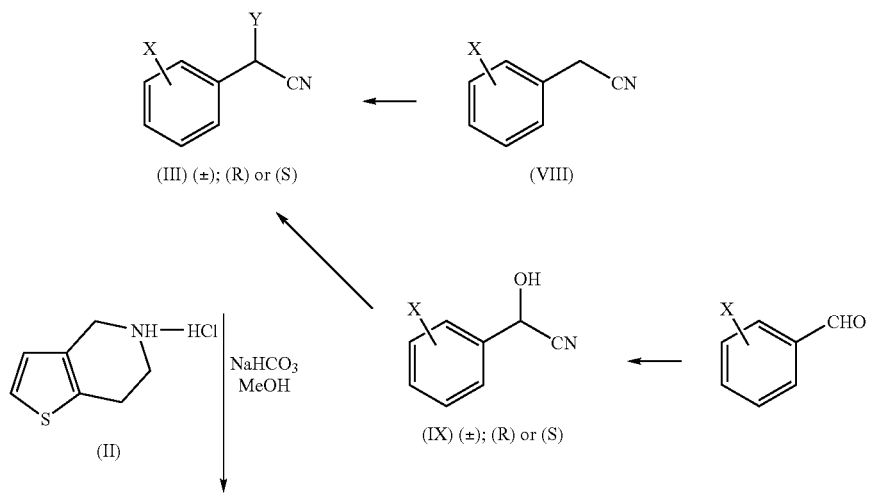

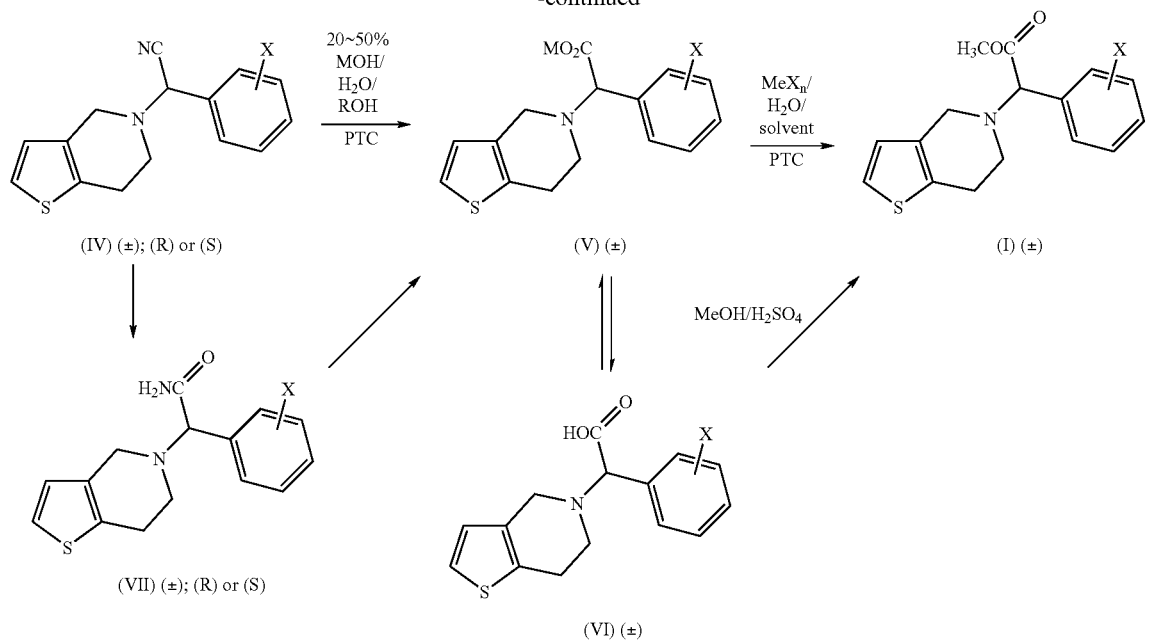
M = K, Na, Ca, Mg etc
ROH C1—C8 etc. alkylic alchol
MeX$_n$ including Me$_2$SO$_4$, MeCl, MeBr, CH$_3$I Me$_3$PO$_4$ etc and other methylation agents
PTC (phase transfer catalysts including quaternary ammonium (phosphonium) salt
PEG 200-3000, crown ethers etc
X = Br, Cl; F, I, etc
Y = Br, Cl; OTs, OMs, OAc etc
Scheme 2 (s)-Resolution of Clopidogrel and of resolution agent
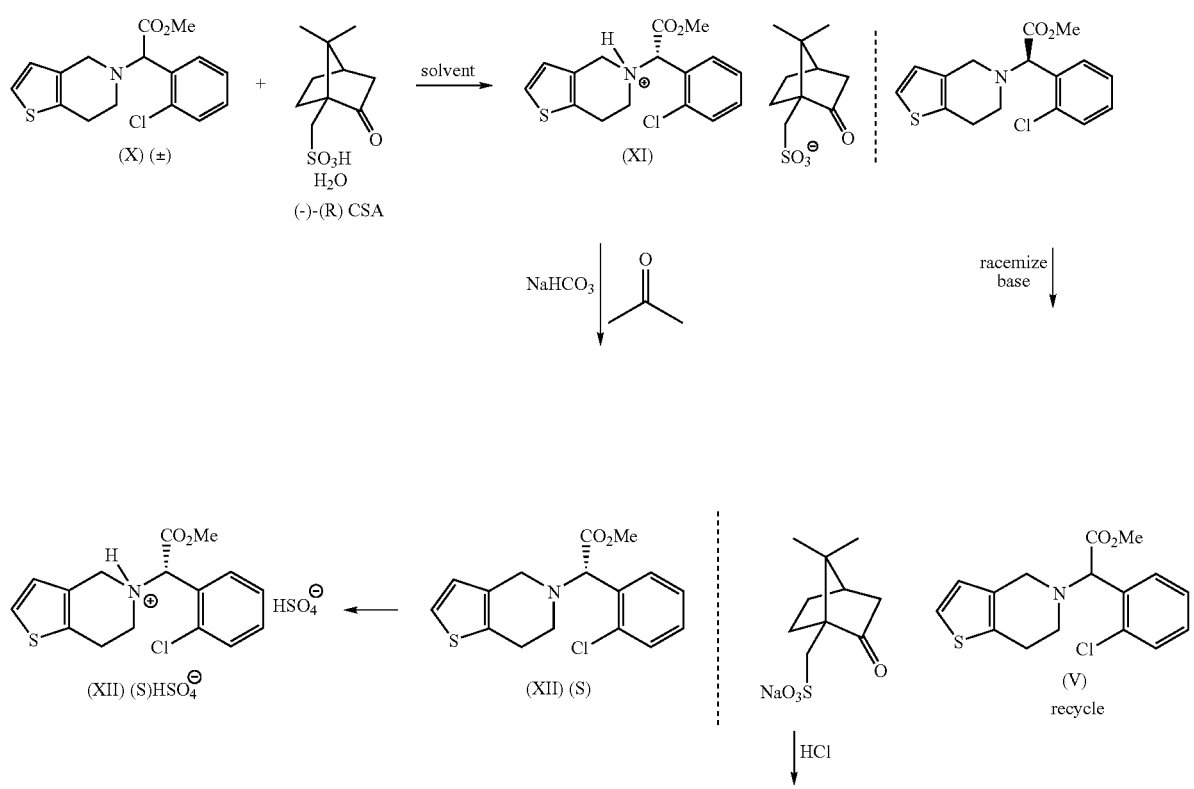

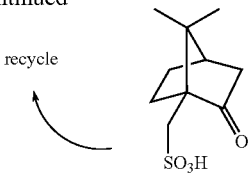

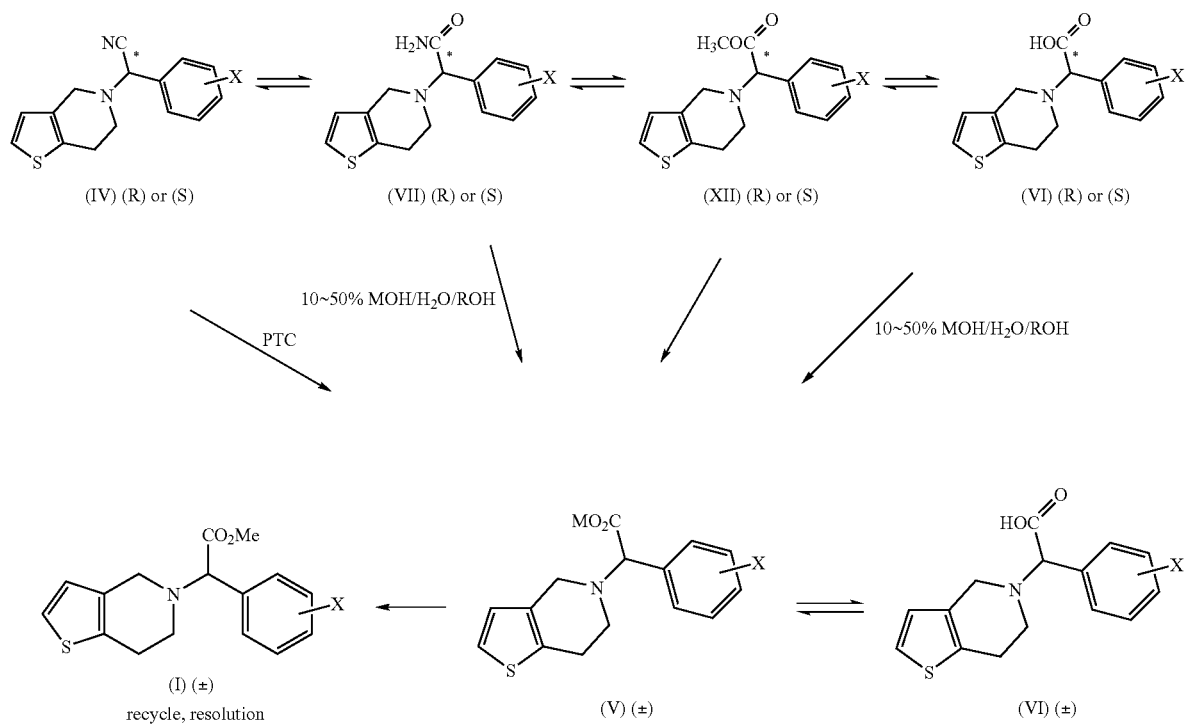

The synthetic route and process for the preparation of Clopidogrel and methyl tetrahydrothienopyridine acetate compounds of formula (I) starting from halogenphenylacetonitrile of formula (VIII) and the key intermediates of tetrahydrothienopyridine acetonitrile of formula (IV) and tetrahydrothienopyridine acetate of formula (V), and the preparation of Clopidogrel and optical active methyl tetrahydrothienopyridine acetate compounds of formula (XII) via kinetic resolution, and at the same time the invention provided the methods for racemization of unwanted optical active enantiomer from unwanted optical active enantiomer of Clopidogrel and its methyl tetrahydrothienopyridine acetate compounds, the recovery and recycled utilization of resolution agents and developed a new synthetic route and new preparation method in a industrial and commercial scale and recyclable, high effective preparation of Clopidogrel (XII) and optical active methyl tetrahydrothienopyridine acetate.

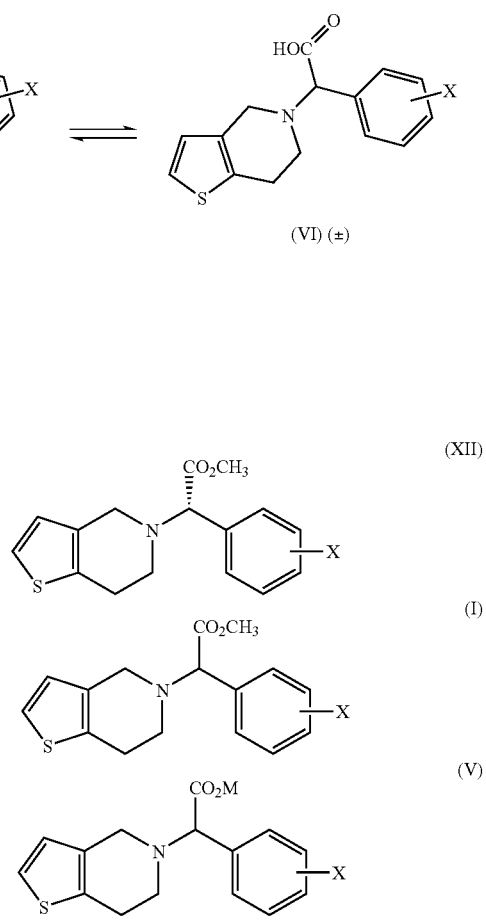

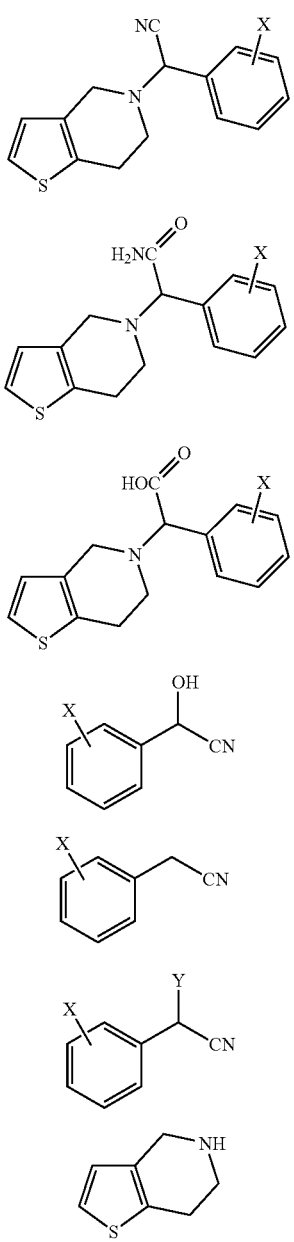

Wherein: X represents hydrogen fluorine, chlorine, bromine or iodine atom; Y represents Br, Cl, or ester group, M represents an alkali metal ion.

The methods and processes presented in this invention are outlined as shown in the following steps comprising:

1) The racemic tetrahydrothienopyridine acetate compound of formula (V) reacts with a methylation agent in aqeuous base catalyzed by a phase transfer catalyst (PTC) in H₂O or an organic solvent or mixtures thereof at 0° C. to 100° C. to form the compounds of formula (I). Compounds of formula (V) can be obtained from the direct alkaline hydrolysis of compounds of formula (IV) in the presence of a strong base and a phase transfer catalyst (PTC) in the mixture of H₂O and organic solvent at 60° C. to 130° C. Compound of formula (IV) can be obtained from the reaction of compound (II) or its salt with compound of formula (III) under alkaline condition in an organic solvent at 0° C. to 110° C. Compound of formula (III) can be obtained from halogenation of compound (VIII) with halogen at 80° C. to 150° C. or derivatived from compound (IX). The reactions from compound of formula (III) to compound of formula (IV), to compound of (V) and further to compound of formula (I) as outlined in scheme 1 can be performed in "one pot" without separation and purification.

2) Racemic Clopidogrel (I) reacts with suitable amount of (R)-(−)camphor sulfonic acid in suitable organic solvent at 0° C. to 120° C. (S)-Clopidogrel kinetically and preferably reacts with (R)-(−)camphor sulfonic acid and precipitates out to realize kinetic resolution as (S)-Clopidogrel camphor sulfonate in the solvent. The precipitated (S)-Clopidogrel camphor sulfonate neutralized with suitable amount of base in a suitable organic solvent, leaving (S)-Clopidogrel free base in organic solvent and the camphor sulfonate is thus separated for its' insolube in organic solvent. R-(−)Camphor sulfonic acid is recycled or reused by further work-up and (S)-Clopidogrel salt (XII) prepared after general work-up.

3) The unwanted enantiomers of Clopidogrel and its tetrahydrothienopyridine analogues of formula (XIII) are hydrolyzed and racemized in 10% to 50% aqueous base and catalyzed by a PTC at 80° C. to 200° C. under pressure of 1 atm to 11 atm. Racemic tetrahydrothienopyridine acetate of formula (V) is thus obtained and the reuse, recycle of the unwanted enantiomers and related intermediates are thus achieved.

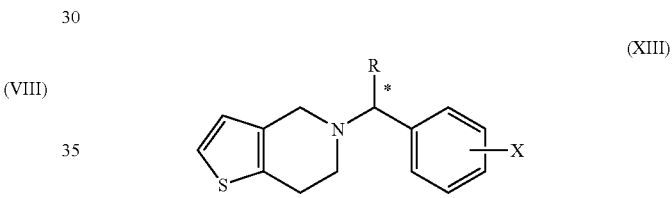

Wherein: R represents —COOH, —CONH₂, —CO₂CH₃ or —CN, X represents hydrogen, fluorine, chlorine, bromine or iodine atom, The methyl tetrahydrothienopyridine acetate of formula (I) mentioned in the present invention can be obtained from methylation of compounds of formula (V) with a methylation agent in H₂O or an organic solvent or mixtures thereof at 0° C. to 100° C. in the alkaline condition catalyzed by PTC.

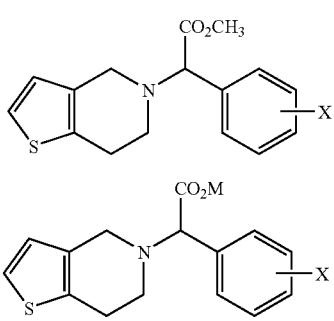

Wherein, X represents hydrogen, fluorine, chlorine, bromine or iodine atom, preferably 2-Cl; M represents an alkali metal ion preferably K or Na.

The mentioned methylation agent can be one of Me₂SO₄, CH₃Cl, CH₃Br, CH₃I, (CH₃O)₃PO₄ etc. The molar ratio of the methylation agent to compounds of formula (V) can be preferably from 1:1 to 5:1 and more preferably from 1:1 to 3:1.

The base used can be one or more than one of optional combinations of NaOH, KOH, NaHCO$_3$, Na$_2$CO$_3$, KHCO$_3$, K$_2$CO$_3$, Et$_3$N, pyridine, N,N-dialkylaniline or sodium alkoxylate. The pH value of the aqueous alkaline solution ranges preferably from 8 to 12, and more preferably from 8 to 10.

The suitable organic solvent can be one or more than one optional combinations of CH$_3$OH, EtOH or C$_1$-C$_8$ alcohols with water; esters such as ethyl acetate, butyl acetate; ketones such as acetone, butanone, methyl isobutyl ketone etc.; aromatic hydrocarbons such as toluene, xylene, polyhalogen substituted benzene; halohydrocarbons such as dichloromethane, chloroform; DMF, DEF, DMSO, THF, DME, dioxane or acetonitrile etc. or mixed solvent thereof. Suitable solvent can be preferably one or more than one optional combinations of methanol, n-butanol or toluene.

The reaction temperature ranges preferably from 30° C. to 80° C.

The reaction is recommended to be catalyzed by a phase transfer catalyst (PTC). The PTC can be selected from one of quaternary ammonium salt, quaternary phosphonium salt, PEG 200-3000, crown ethers and the like. The suitable PTC can be preferably one or more than one optional combinations of benzyltriethylammonium chloride, PEG400, PEG600 or PEG800. The amount of the PTC is 0.5% to 5% weight of tetrahydrothienopyridine acetate of formula (V) used. The compounds of general formula (I) may react with suitable amount of sulfuric acid to form its bisulfate.

Alternatively, the compound of formula (VI) can be easily obtained from compound of formula (V) just by adjusting pH value of the solution to 4-5, compounds of formula (I) can also be obtained from esterification of compounds of formula (VI) in methanol catalyzed by a suitable catalyst selected from concentrated sulfuric acid, fuming sulfuric acid, methanesulfonic acid, strong acid resin and sodium (potassium) bisulfate etc, or obtained from compound (VI), reacted with slightly excessive acyl halides such as SOCl$_2$, PX$_3$, PX$_5$, POCl$_3$, or ClCO$_2$R (X=Cl, Br etc.) in at least one molar methanol and suitable additional solvents at 0° C. to 100° C. The suitable additional solvents may be selected from one of esters such as ethyl acetate, butyl acetate; ketones such as acetone, butanone, methyl isobutyl ketone; toluene, xylene, or (poly)chloro (substituted) benzene or dichloromethane, dichloroethane, chloroform; DMF, DEF, DMSO, THF, DME, dioxane, acetonitrile or mixtures thereof. The most preferable solvent is methanol. It is also possible to transform compound of formula (VI) to its acyl halide or (mixed) anhydride and further to react with methanol at 0° C. to 100° C., preferably 0° C. to 70° C. to prepare the chloride of formula (X) and get the compound of formula (I) after simple neutralization.

The compound of formula (I) can also be obtained from other related and similar reactions after recovery of methanol and excess amount of acyl halide reagent, and treated by routine method. The unreacted compound of formula (VI) can be recycled or reused by simple acid and base neutralization and further purification if required.

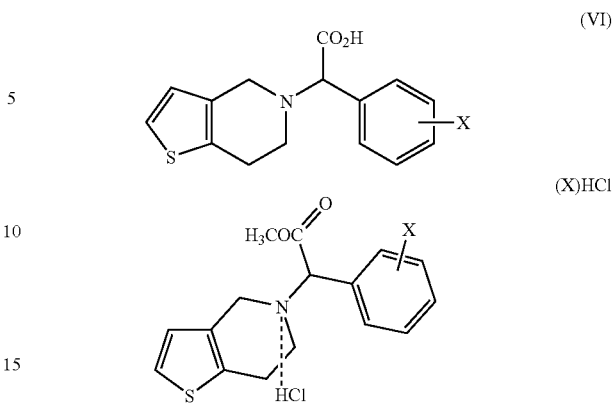

Optionally, compound of formula (I) can also be obtained from the methylation of compounds of formula (V) or compounds of formula (VI) in suitable solvents in the presence of a base and a PTC at suitable temperature. The suitable base used can be one of Na$_2$CO$_3$, NaHCO$_3$, K$_2$CO$_3$, KHCO$_3$, NaOH, KOH, Et$_3$N, pyridine, N,N-dialkylaniline, sodium alkoxylate or mixtures thereof and the like. Suitable solvents used can be selected from one of H$_2$O, CH$_3$OH, EtOH or C$_1$-C$_8$ alcohols or mixtures thereof and the like; esters such as ethyl acetate, butyl acetate; ketones such as acetone, butanone, methyl isobutyl ketone; toluene, xylene or (poly) chloro (substituted) benzene etc. or halogen substituted solvents such as dichloromethane, chloroform; DMF, DEF, DMSO, THF, DME, dioxane, acetonitrile or mixtures thereof and the like. The temperature ranges from 0° C. to 100° C., preferably from 30° C. to 80° C. The methylation agents used can be one of Me$_2$SO$_4$, CH$_3$Cl, CH$_3$Br, CH$_3$I, (CH$_3$O)$_3$PO$_4$ and the like. The pH value of the solution ranges preferably from 8 to 12, and more preferably from 8 to 10. PTC can facilitate the methylation and the suitable PTC can be selected from one of quaternary ammonium salt, quaternary phosphonium salt, PEG 200-3000 (the molecular weight is 200-3000) and crown ethers and the like, preferably benzyltriethylammonium chloride, PEG400, PEG600, or PEG800. The pH value is not required if the reaction is taken in nonaqueous or homogeneous mixture of water-organic solvent. The molar ratio of the base to compound of formula (VI) ranges preferably from 1:1 to 3:1, more preferably from 1:1 to 1.5:1. It is also another option to transform compound of formula (VI) to compound of formula (V) with the mentioned base in the mentioned or other solvents. The unreacted compound of formula (VI) can be recycled or reused by simple acid and base neutralization and after tested to prove the quality met the requirement of standards.

Another objective of the present invention is to provide a novel synthetic route and process for preparing the optical active or the racemic intermediates of mentioned methyl tetrahydrothienopyridine acetate compounds The process for the above preparation of compound of formula (V), wherein, the direct alkaline hydrolysis of compound of formula (IV) is performed in the presence of 20% to 50% base and a PTC in the mixture of H$_2$O and organic solvent at 60° C. to 130° C.

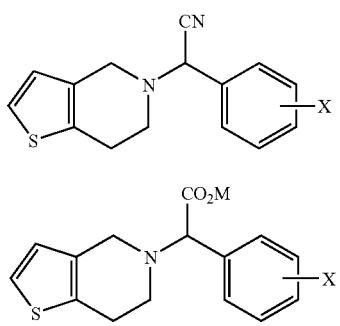

Wherein: X represents fluorine, chlorine, bromine or iodine atom, preferably 2-Cl;

PTC is indispensable for such a direct hydrolysis. The direct hydrolysis can not proceed or the yield of compound of formula (V) is too poor to be of value if without PTC. The suitable PTC in the process of converting compounds of formula (IV) to compounds of formula (V) can be selected from one of quaternary ammonium salt, quaternary phosphonium salt, PEG 200-3000 (the molecular weight is 200-3000) and crown ethers and the like. The PTC can be preferably benzyltriethylammonium chloride (TEBA), PEG400, PEG600 or PEG800. The weight loading of which can be from 0.1% to 10% of compounds of formula (IV) used, preferably from 0.5% to 5%.

The suitable organic solvent is selected from one or one or more than one optional combinations of $C_1$-$C_8$ alcohols, preferably methanol, ethanol or n-butanol, most preferably n-butanol.

The concentration of the base is critical to the direct hydrolysis. The yield of compounds of formula (V) is generally poor if the concentration of the aqueous sodium hydroxide or potassium hydroxide or mixtures thereof is less than 20%. The greater the concentration of base is, the more sufficient the hydrolysis is. The concentration of the aqueous sodium hydroxide or potassium hydroxide or their mixtures ranges preferably from 35% to 50%. The molar ratio of the mentioned base to compounds of formula (IV) ranges from 1:1 to 20:1, preferably from 15:1 to 20:1. The hydrolysis reaction temperature ranges preferably from 90° C. to 120° C.

Both the key intermediates of optical active isomers and the racemic compounds of formula (V) can be obtained from the method described above based on controlling the starting materials used.

The present invention also provides another method for preparing the compounds of formula (V) from compounds of formula (VII) is by alkaline hydrolysis in 20% to 50% aqueous base catalyzed by a PTC at 80° C. to 200° C. under pressure of 1 atm to 11 atm.

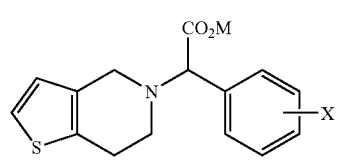

Wherein: X represents atoms of hydrogen or fluorine, chlorine, bromine or iodine, preferably 2-Cl; M represents an alkali metal ion, preferably sodium or potassium ion.

The PTC used in the transformation of compounds of formula (VII) to compounds of formula (V) can be selected from one of quaternary ammonium salt, quaternary phosphonium salt, PEG 200-3000 (the molecular weight is 200-3000) and crown ethers and the like or mixtures thereof. The PTC can be preferably one of benzyltriethylammonium chloride, PEG400, PEG600 or PEG800. The weight loading of which ranges from 0.1% to 10% of reaction compounds of formula (VII), preferably from 0.5% to 5%.

The mentioned alkaline hydrolysis is performed in the presence of organic solvent. The suitable organic solvent can be one or more than one optional combinations of $C_1$-$C_8$ alcohols, preferably methanol, ethanol or n-butanol, and most preferably n-butanol.

The concentration of the base is critical to the hydrolysis. The concentration of the aqueous sodium hydroxide or potassium hydroxide or their mixture ranges preferably from 35% to 50%. The molar ratio of the mentioned base to compounds of formula (VII) ranges preferably from 1:1 to 20:1, and more preferably from 15:1 to 20:1.

The pressure used in the alkaline hydrolysis means the absolute pressure, and ranges preferably from 1 atm to 3 atm. The suitable temperature of such a reaction ranges preferably from 90° C. to 120° C.

The tetrahydrothienopyridine acetate salt of compound (V) mentioned in the present invention can also be easily obtained from the neutralization of compounds of formula (VI) with a suitable base.

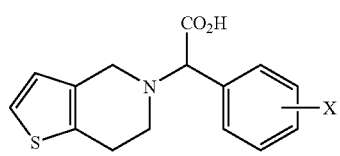

Wherein: X represents atoms of hydrogen fluorine, chlorine, bromine or iodine, preferably 2-Cl.

The present invention also provides a process for preparing the above mentioned compounds of formula (IV) by reacting compounds of formula (II) or its salt (preferably hydrochloride or sulfate) with compounds of formula (III) in $H_2O$ or in a suitable organic solvent or their mixtures in the presence of a base at 0° C. to 110° C.

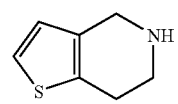

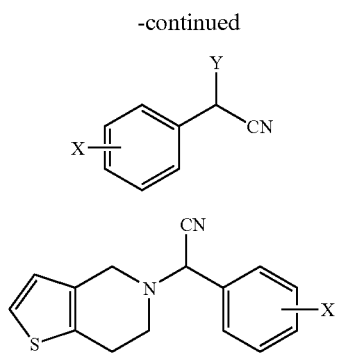

(III)

(IV)

Wherein: X represents atoms of hydrogen, fluorine, chlorine, bromine or iodine preferably 2–Cl; Y represents Br, Cl, and ester group, preferably Br or Cl, more preferably Br; the ester group can be preferably one of p-toluene sulfonyl, p-nitrobenzene sulfonyl, benzene sulfonyl, methyl sulfonyl or acetoxyl group.

Suitable solvents used can be one of ethyl acetate, butyl acetate; ketones such as acetone, butanone, methyl isobutyl ketone; toluene, xylene, poly-halogen substituted benzene or halogenalkane such as dichloromethane, dichloroethane, chloroform; DMF, DEF, DMSO, THF, DME, dioxane, acetonitrile; $C_1$-$C_4$ alcohols such as $CH_3OH$, EtOH, n-butanol or mixtures thereof, more preferably one of methanol, n-butanol or mixtures thereof.

The reaction is performed in the presence of a base. The suitable base used can be one or more than one of NaOH, KOH, $NaHCO_3$, $Na_2CO_3$, $KHCO_3$, $K_2CO_3$, $Et_3N$, pyridine, N,N-dialkylaniline, sodium alkoxylate, preferably $NaHCO_3$. The molar ratio of the base to the compounds of formula (III) ranges from 1:1 to 5:1.

The reaction is carried out preferably at 50° C. to 80° C. in generally more than 85% yield Both the optical active isomers and the racemic compounds of formula (IV) can be obtained by the method described above based upon the control of starting materials used.

Some of the compounds of formula III (if Y=Br or Cl) can be prepared from the corresponding compounds of formula (VIII) by halogenation with a halogen at 80° C. to 150° C.

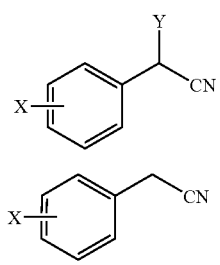

(III)

(VIII)

X represents atoms of hydrogen fluorine, chlorine, bromine or iodine, preferably 2–Cl; Y represents bromine or chlorine atoms.

The halogenation temperature ranges preferably from 100° C. to 130° C.

The molar ratio of the halogen to the compounds of formula (VIII) can be preferably from 0.5:1 to 1.5:1, and more preferably from 0.9:1 to 1.2:1.

The high content of substituted phenylacetonitrile compounds of formula (III) can be easily obtained by the method described above after halogenation just by washing, layer separation and general work-up without further purification.

The compounds of formula (III), (if Y=ester group) can be prepared from compounds of formula (IX) with a suitable esterification agent under the alkaline condition in $H_2O$ or organic solvent at 0° C. to 100° C. The esterification agent can be selected from sulfonyl choride, acyl choride, acid anhydride, organic acids.

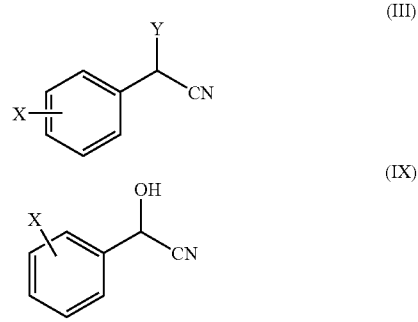

(III)

(IX)

X represents atoms of hydrogen, fluorine, chlorine, bromine or iodine, preferably 2–Cl; Y represents ester group, the preferable ester group can be one of following: p-toluene sulfonyl, p-nitrobenzene sulfonyl, benzene sulfonyl, methyl sulfonyl, or acetoxyl group.

The suitable esterification agent can be selected from one of p-toluene sulfonyl chloride, 4-nitrobenzene sulfonyl chloride, benzene sulfonyl choride, methyl sulfonyl chloride, acetyl chloride, acetic anhydride or acetic acid. The molar ratio of esterification agent to the compounds of formula (IX) range from 1:1 to 3:1, preferably from 1:1 to 1.2:1.

Suitable solvents used can be one or more than one optional combinations of ethyl acetate, butyl acetate, acetone, butanone, methyl isobutyl ketone; toluene, xylene, chlorobenzene, dichloromethane, dichloroethane, chloroform, DMF, DEF, DMSO, THF, DME, dioxane, or acetonitrile. The preferable organic solvent can be one of butyl acetate, toluene, xylene, chlorobenzene, acetonitrile or mixtures thereof.

The reaction is performed in the presence of a base. The suitable base can be one or more than one optional combination of NaOH, KOH, $NaHCO_3$, $Na_2CO_3$, $KHCO_3$, $K_2CO_3$, $Et_3N$, pyridine, N,N-dialkylaniline, preferably NaOH, KOH, $Et_3N$, N,N-dimethylaniline or mixtures thereof. The molar ratio of the base to compounds of formula (IX) can be from 1:1 to 5:1.

The preferable esterification temperature ranges from 0° C. to 30° C.

All the reactions and processes provided in the present invention, every intermediate can be used directly in preparation of next compound, or can be taken in following steps after separation and purification. For example, compounds of formula (I) can be obtained either directly from the reaction solution of compounds of formula (V), or prepared after separation and purification of compounds of formula (V), and then use it to prepare compound (I). Moreover, either optical active or racemic key intermediates (III), (IV), (V) and (VI) isomers can be obtained by the method described above based upon the control of starting materials used.

The present invention also provides some effective processes for the kinetic resolution of racemic Clopidogrel, for the recovery and recycle of (R)-(–)Camphor sulfonic acid which comprising in the following steps:

(1) Racemic Clopidogrel (I) reacts with R-(−)Camphor sulfonic acid in suitable organic solvent at 0° C. to 120° C. (S)-Clopidogrel isomer preferably and kinetically reacts with R-(−)Camphor sulfonic acid and precipitates out as the (S)-Clopidogrel camphor sulfonate in the suitable solvent to realize kinetic resolution.

(2) The so obtained (S)-Clopidogrel camphor sulfonate neutralized with a suitable base in a suitable organic solvent and (S)-Clopidogrel free base is left in organic solvent while camphor sulfonate precipitated out for its insolubility in organic solvent and thus to achieve the separation and preparation of (S)-Clopidogrel salt of (XII) and recycle of R-(−) camphor sulfonic acid after general work-up.

The suitable organic solvent used in step (1) can be one of benzene, toluene, xylene, cholorbenzene, dichlorobenzene, dichloromethane, 1,2-dichloroethane, chloroform, tetrachloromethane, ethyl acetate, butyl acetate, isopropanol, butanol; preferably toluene, xylene, cholorbenzene, dichlorobenzene, ethyl acetate, butyl acetate or isopropanol more preferably toluene, xylene or isopropanol, and most preferably toluene.

The molar ratio of R-(−)camphor sulfonic acid to racemic Clopidogrel ranges from 0.2:1 to 0.8:1, preferably from 0.2:1 to 0.6:1, more preferably from 0.45:1 to 0.55:1.

The reaction temperature in step (1) ranges preferably from 15° C. to 50° C.

(S)-Clopidogrel camphor sulfonate prepared according to the process of step (1) can be facilitate precipitated out if some crystal seeds added.

The (S)-Clopidogrel camphor sulfonate precipitated in step (1) can be further purified by washing or recrystallization in a suitable solvent. The suitable solvent for washing or recrystallization can be one or more than one of optional combinations of: toluene, xylene, cholorbenzene, dichlorobenzene, ethyl acetate, butyl acetate, isopropanol, preferably isopropanol or butyl acetate. The weight (g) and volume (ml) ratio of substrate to solvent can range from 1:1 to 1:6, and preferably from 1:1 to 1:2. The purification temperature ranges from 25° C. to the refluxing temperature of the solvent used, preferably from 40° C. to 110° C. The washing time is generally more than thirty minutes.

The transformation mentioned in step (2) is well known or understood by general technicians in the related field and the reaction can be easily carried out by referring to the reported method in U.S. Pat. No. 6,737,411B2 or other literatures. In all the reported methods, the reaction is always performed in aqueous phase system, and thus cause the recover of the easily water soluble chiral resolution agent (R)-(−)camphor sulfonic acid or its sodium salt very difficult. On the other hand, methyl ester of Clopidogrel is liable to be hydrolyzed in alkaline solution. Therefore, the present invention also provides an effective process for such a transformation in organic solvent and an economical recover or reuse of the chiral resolution agent ((R)-(−)camphor sulfonic acid).

The obtained (S)-Clopidogrel camphor sulfonate reacts with a suitable base in a suitable organic solvent and (S)-Clopidogrel free base is remain soluble in organic solvent while (R)-camphor sulfonate precipitated out due to its reduced solubility in organic solvent and thus to achieve the separation of (S)-Clopidogrel free base and (R)-(−)camphor sulfonic acid salt and the reuse of (R)-(−)camphor sulfonic acid The obtained (S)-Clopidogrel free base by the above method may be easily transformed to its salt by reacting with a suitable acid and the filtrate obtained from (S)-Clopidogrel free base can also react with acid to obtain salt of (S)-Clopidogrel.

The base used in step (2) can include one of inorganic base such as $NaHCO_3$, $Na_2CO_3$, $KHCO_3$, $K_2CO_3$, CaO, $Ca(OH)_2$ etc. Organic base such as $Et_3N$, N,N-dimethylaniline, pyridine, NaOAc, KOAc, sodium alkoxylate or mixtures thereof; preferably $NaHCO_3$, $KHCO_3$, $Et_3N$, N,N-dimethylaniline, NaOAc, KOAc or sodium alkoxylate. The molar ratio of base to (S)-Clopidogrel camphor sulfonate ranges preferably from 1:1 to 1.5:1.

The organic solvents used during such a transformation in step (2) can include one of $C_1$-$C_8$ alcohols such as methanol, ethanol, isopropanol and butanol; ketones, such as acetone, butanone, methyl isobutyl ketone; esters such as ethyl acetate, butyl acetate; aromatic hydrocarbon such as toluene, xylene, chlorobenzene, dichlorobenzene or mixtures thereof. The preferable solvent can be one of methanol, ethanol, isopropanol, butanol, acetone, butanone, methyl isobutyl ketone, ethyl acetate, butyl acetate, toluene, xylene, chlorobenzene and dichlorobenzene or mixtures thereof. The weight (g) and volume (ml) ratio of (S)-Clopidogrel-(R)-(−)camphor sulfonate to the organic solvent can be preferably from 1:1 to 1:6, and more preferably from 1:3 to 1:5.

The transformation reaction mentioned in the present invention is generally performed at refluxing temperature of the solvent used for more than 3 hours. After the reaction is completed, the solution is cold to 0° C. to 15° C., the residue is treated by filtration and washing. The (S)-Clopidogrel free base stays in the filtrate and the organic solvent insoluble solid (mainly, camphor sulfonate and excessive base) is separated. The filtrate reacts with equal moles acid to give the desired (S)-Clopidogrel salt. The acid used in this process can be one of hydrochloric acid, hydrobromic acid, concentrated sulfuric acid etc (R)-camphor sulfonate reacts with a suitable acid in an organic solvent to achieve the recovery and recycle of camphor sulfonic acid. The suitable organic solvent includes one of $C_1$-$C_8$ alcohols such as methanol, ethanol, isopropanol and butanol; ketones such as acetone, butanone, methyl isobutyl ketone; esters such as ethyl acetate, butyl acetate etc. The suitable acid used in this process can be one of hydrogen chloride gas, hydrogen bromide gas, concentrated sulfuric acid, nitric acid, phosphoric acid and the like if desired or their high concentrated aqueous solutions thereof, in more than one mole or by adjusting the system pH value to about 1.

The chiral resolution methods and the processes provided in the present invention are simple and highly effective with less and recyclable chiral resolution agent in single and cheap solvent with excellent enatioselectivity (>99% ee). The whole process is environmental protective and cost effective industrially and commercially reliable.

The tetrahydrothienopyridine derivatives of formula (XIII) mentioned in this invention. The recemization of enantiomers of these compounds are comprising following steps: The optical active isomers are hydrolyzed in 10% to 50% alkaline solution, catalyzed by a PTC at 80° C. to 200° C. under the pressure of 1 atm to 11 atm to form the racemic tetrahydrothienopyridine acetate of formula (V).

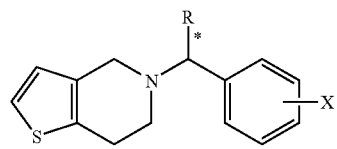

(XIII)

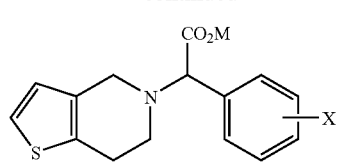

(V)

Wherein: R represents —COOH, —CN, COCH₃, —CONH₂. M represents an alkali or an alkali earth metal ion such as K, Na, Ca, Mg, preferably Na or K ion.

The PTC used in the transformation can be selected from one of quaternary ammonium salt, quaternary phosphonium salt, PEG 200-3000 (the molecular weight is 200-3000), crown ethers. The preferable PTC can be one of benzyltriethylammonium chloride, PEG400, PEG600, or PEG800. The weight of catalyst used in the reaction can be from 0.1% to 10% of compounds of formula (XIII), preferably from 0.5% to 5%.

The mentioned alkaline hydrolysis and racemization process can be carried in either water or organic solvent or in a mixture of water and an organic solvent. Organic solvent in which the resulting product is soluble can facilitate the reaction of alkaline hydrolysis. The suitable organic solvent is selected from one of $C_1$-$C_8$ alcohols or mixtures thereof, preferably one or more than one of optional combination of methanol, ethanol, n-butanol, and most preferably n-butanol. The volume of the organic solvent used is generally from 1 ml to 5 ml per gram of the compounds of formula (XIII) used.

The mentioned basic water solution preferably the solution of sodium hydroxide or potassium hydroxide or mixtures thereof, the concentration ranges from 35% to 50%. The molar ratio of the base to compounds of formula (XIII) ranges preferably from 1:1 to 20:1, and more preferably from 15:1 to 20:1.

The alkaline hydrolysis temperature ranges preferably from 90° C. to 120° C.

For complete and sufficient racemization of the optical active R or S isomer used in the alkaline hydrolysis, it is necessary to elevate the reaction temperature and pressure, prolong the reaction and racemization time or increase the concentration of the base.

The suitable pressure ranges from 1 atm to 11 atm, preferably from 1 atm to 3 atm, and the reaction time can be preferably from 2 to 72 hours.

Summarily, the racemization of the present invention includes the following steps:

Optical active compounds of formula (XIII) is racemized in 35% to 50% aqueous base catalyzed by a PTC under the pressure of 1 atm to 3 atm at 90° C. to 120° C. for 2 to 72 hours to give racemic compounds of formula (V).

Compounds of formula (V) can be transformed to compounds of formula (VI) by simple acidification.

The present invention also provides a process for preparing the racemic compounds of formula (V) by alkaline hydrolysis and racemization of optical active compounds of formula (XII) in mild condition and relatively lower concentration base. Such a hydrolysis and racemization is taken in 5% to 50% alkaline solution in the presence of a PTC under the pressure of 1 atm to 11 atm at 80° C. to 200° C. The final product is the racemic compounds of formula (V).

The suitable base used in the alkaline hydrolysis and racemization of compounds (XII) can be one of 5% to 50% of NaHCO₃, Na₂CO₃, KHCO₃, K₂CO₃, NaOH, KOH or mixtures thereof. It is possible that the obtained compounds of formula (V) can be partly racemized in such a mild reaction condition when 5% to 15% aqueous base is used.

The other conditions for the alkaline hydrolysis and racemization are the same as those described for compound (XIII).

Similarly, compounds of formula (V) can be transformed to compounds of formula (VI) just by simple acidification.

This invention firstly realized the novel method for preparation and kinetic resolution of methyl-tetrahydrothienopyridine acetate compounds with racemic Clopidogrel as representative and also the method for racemization and recycle for comprehensive utilization of unwanted chiral compounds. These provide an economical reliable and efficient way to get the target chiral compounds and simultaneously resolve problems of non-environmental protective disposal (storage) of unwanted chiral "wastes" and recovery and recycle utilization of chiral resolution agents, and remarkably enhance the efficiency and economical effect of preparation of methyl-tetrahydrothienopyridine acetate analogous with Clopidogrel as representative.

Wholly, the present invention provides a novel synthetic route and process for preparing the compounds of formula (XII) and related optical active chiral isomers and racemic key intermediates of compounds of formula (XIII). The so provided methods and processes are simple, mild, easily operated, less poisonous materials and solvents used and environmental protective, and the starting materials are cheap and commercially available. Furthermore, all these conversions or reaction steps can be taken separately (above 80% yield for every conversion) or in one-pot without any strict separation or purification of any intermediate. Both ways can give the same high total yield.

The kinetic resolution methods and the processes provided simple and high effective with less and recyclable chiral resolution reagent in simple and cheap solvent with excellent enantioselectivity (>99% ee). The whole process is environmental protective and cost effective, and it can be applied to both industrial and commercial production.

The present invention also provides an easy operated process of racemization, recover of the unwanted chiral compounds and the recycle, reuse of the chiral resolution agent.

The invention provides a method to resolve problems of non-environmental protective disposal (storage) of unwanted chiral "wastes" via the resolution of racemic compounds or racemization, transformation and utilization of unwanted chiral compounds or intermediates. The technology is simple and easy to operate, and can be used in industrialized production with environmental protective advantages.

EMBODIMENTS OF THE INVENTION

In order to describe this invention thoroughly, the preparation methods are verified by following examples. These examples are only used for illustration and therefore should not be construed as limitations to the scope of the invention.

EXAMPLES

Example 1

Preparation of (±)-methyl-(2-chlorophenyl)-(4,5,6,7-4H-thieno[3,2,-c]pyrid-5-yl) acetate (I)

The mixture of (±)-(2-chlorophenyl)-(4,5,6,7-4H-thieno [3,2,-c]pyrid-5-yl) acetonitrile (60 g, 0.208 mol), aqueous KOH (40%, 360 g, 3.6 mol), n-butanol (200 mL) and TEBA (1.2 g, 0.005 mol as PTC) was refluxed for about 8 hours (about 115° C.). After cooling to room temperature, the solution was neutralized with aqueous HCl (ca 20%) to pH about 11 and $H_2O$ was added with stirring till the solid was dissolved. Ethyl acetate (50 mL×2) was added to extract and remove small amount of incomplete hydrolyzed amide (intermediate) (may be recycled). The pH of the aqueous solution is re-adjusted to 9. n-Butanol (100 mL) was added to the aqueous solution and $Me_2SO_4$ (120 g, 0.952 mol) was added dropwise for about half an hour at room temperature. After the addition was finished, the reaction was kept at room temperature for two hours with constant adjusting to keep the pH at 9 and heat to 45□ for reaction more than eight hours. The reaction was refluxed for another two hours. After cooling to room temperature, the organic phase was separated and the aqueous solution was extracted with butanol (50 ml×2), the combined organic solution was washed with water, dried and evaporated to remove solvent. The high purity crude Clopidogrel was obtained in 40% total yield. The oily racemic Clopidogrel free base reacts with 98% sulfuric acid in suitable amount of acetone giving the racemic Clopidogrel bisulfate.

The unreacted acid in the water layer can be recovered and reused for times according to the following procedure:

The aqueous solution was finely adjusted to pH 4-4.5 and the acid was precipitated out after cooling at low temperature. The high purity acid, obtained after routine de-salting and purifying the crude acid by washing with water or recrystallization, can be reused for esterification for times. Because the acid is fairly soluble in n-butanol; it is recommended to extract the acid with n-butanol as the follows: After adjusting the pH of the aqueous layer to 4-4.5, n-butanol and suitable amount of water were added (to make the salt dissolved), the solution was heated and extracted. After cooling to 10° C. the n-butanol layer was separated and the aqueous solution was extracted with n-butanol again. The combined organic solvent was evaporated under reduced pressure to give the pure acid for reuse

Example 2

Preparation of (±)-methyl-(2-chlorophenyl)-(4,5,6,7-4H-thieno[3,2,-c]pyrid-5-yl) acetate (I)

The mixture of (±)-(2-chlorophenyl)-(4,5,6,7-4H-thieno[3,2,-c]pyrid-5-yl) acetonitrile (60 g, 0.208 mol), aqueous NaOH (40%, 360 g), methanol (100 mL), TEBA (1.0 g, 0.00439 mol as PTC) was refluxed in a suitable reaction flask for about 12 hours. After cooling to room temperature, the mixture was filtered and the (±)-(2-chlorophenyl)-(4,5,6,7-4H-thieno[3,2,-c]pyrid-5-yl) sodium acetate (V) was obtained (63 g, yield 94.1%).

The so obtained (±)-(2-chlorophenyl)-(4,5,6,7-4H-thieno[3,2,-c]pyrid-5-yl) sodium acetate (63 g, 0.191 mol), $H_2O$ (250 mL), TEBA (1.2 g, 0.005 mol as PTC) was mixed and adjusted to about pH 10 with aqueous NaOH, and toluene (200 mL) was added. $Me_2SO_4$ (120 g, 0.952 mol) was added dropwise at 10° C. The reaction was stirred at room temperature for 5 hours and at 40□ for 26 hours in constant keeping of the pH value of the solution to about 10 during the reaction. After the reaction was completed, the organic layer was separated, and the water layer was extracted with butyl acetate for times. The combined organic layer was washed with water and dried. After evaporating the solvent under reduced pressure, the oily target product was obtained (32 g, 51% yield).

Example 3

Preparation of (±)-methyl-(2-chlorophenyl)-(4,5,6,7-4H-thieno[3,2,-c]pyrid-5-yl) acetate (I)

(±)-(2-Chlorophenyl)-(4,5,6,7-4H-thieno[3,2,-c]pyrid-5-yl) sodium acetate (63 g, yield 94.1%) was prepared according to the method described in example 2.

(±)-(2-chlorophenyl)-(4,5,6,7-4H-thieno[3,2,-c]pyrid-5-yl) sodium acetate (63 g, 0.191 mol), $H_2O$ (250 mL), PEG 400 (1.5 g, 0.00375 mol as PTC) was mixed and adjusted to about pH 10 with $NaHCO_3$ and n-butanol (200 mL) was added. $Me_2SO_4$ (120 g, 0.952 mol) was added dropwise at 10° C. The reaction mixture was stirred at room temperature for 5 hours and at 40° C. for 26 hours in constant keeping of the pH value of the solution to about 10 during the reaction. After the reaction was completed, the organic layer was separated, and the water layer was extracted with butyl acetate. The combined organic layer was washed with water and dried. The organic solvent was removed under reduced pressure. The oily target product was obtained (32 g, 51% yield).

Example 4

Preparation of (±)-methyl-(2-chlorophenyl)-(4,5,6,7-4H-thieno[3,2,-c]pyrid-5-yl) acetate (I)

(±)-(2-chlorophenyl)-(4,5,6,7-4H-thieno[3,2,-c]pyrid-5-yl) sodium acetate (V) (63 g, yield 94.1%) was prepared according to the method described in example 2.

The mixture of (±)-(2-chlorophenyl)-(6,7-4H-thieno[3,2,-c]pyrid-5-yl) sodium acetate (63 g, 0.191 mol), aqueous NaOH (20%, 60 g), TEBA (1.2 g, 0.0053 mol as PTC dissolved in 250 ml methanol) was refluxed with stirring for about half an hour, cooled to about 10° C. and $Me_2SO_4$ (40 g, 0.317 mol) was added dropwise slowly. The reaction mixture was warmed up to 20° C. to 25° C. to react for 2 hrs and for 12 hrs at 40□. After reaction was completed, methanol was recovered, and then 50 mL butyl acetate was added, the organic layer was separated and washed times with water and dried, evaporated under reduced pressure to remove butyl acetate and finally afford the oily Target product (28 g, 47% yield).

Example 5

Preparation of (±)-methyl-(2-chlorophenyl)-(4,5,6,7-4H-thieno[3,2,-c]pyrid-5-yl) acetate (I)

The same reaction conditions as described in example 2, while n-butanol instead of toluene as solvent, and the oily target product was obtained (26 g, 44% yield).

Example 6

Preparation of (±)-methyl-(2-chlorophenyl)-(4,5,6,7-4H-thieno[3,2,-c]pyrid-5-yl) acetate (I)

The same reaction conditions as described in example 3, while toluene as solvent and the oily target product was obtained (28 g, 47% yield).

Example 7

Preparation of (±)-methyl-(2-chlorophenyl)-(4,5,6,7-4H-thieno[3,2,-c]pyrid-5-yl) acetate (I)

The same conditions as described in example 3 except that the PTC was 18-crown-6 (0.4 g, 0.00127 mol), and the oily target product was obtained (30 g, 50% yield).

Example 8

Preparation of (±)-methyl-(2-chlorophenyl)-(4,5,6,7-4H-thieno[3,2,-c]pyrid-5-yl) acetate (I)

(1) Preparation of (±)α-Bromo-2-(2-chlorophenyl) acetonitrile 2-(2-Chlorophenyl) acetonitrile (151.5 g, 1 mol) was heated to 110° C. in a three-necked flask, keep the temperature, bromine (176 g, 1.1 mol) was added dropwise over a period of 3 h and the mixture was reacted with constant stirring for another 3 h. The reaction mixture was cooled to below 30° C. and water (400 mL) was added and stirring continued for another 5 minutes to remove HBr and stand aside. The organic layer was separated and washed with small amount of 5% sodium bisulfite for 15 minutes with stirring. The organic layer was again separated and washed with water to near pH 7, and the brown oily product was obtained (225 g, 96% yield); bp: 107-110° C./15 mmHg. IR (cm$^{-1}$): 2969, 2253, 1589, 1472, 1445, 1194, 1051, 765, 725, 646; $^1$HNMR (300 MHz, CDCl$_3$): 7.83 (1H, m), 7.38-7.45 (4H, m), 5.87 (1H, s). The crude product was used directly for the next step.

(2) Preparation of (±)-(2-chlorophenyl)-(4,5,6,7-4H-thieno[3,2,-c]pyrid-5-yl) acetonitrile (IV)

α-Bromo-2-(2-chlorophenyl) acetonitrile (98.65 g, 0.428 mol) obtained as above, sodium hydrogen carbonate (84 g, 1.0 mol) and 4,5,6,7-tetrahydrothieno[3,2-c]pyridin-5-ium chloride (70.2 g, 0.4 mol) dissolved in methanol (300 mL) in a suitable reaction flask. The mixture was stirred and refluxed for more than 3 h until the material was completed by TLC test until the main spot of raw material was disappeared. The mixture was cooled to 0° C. to 5° C., filtered, the filter cake was washed with water by stirring thoroughly, then washed with cold methanol, and dried to give pale yellow fine granular solid product (98 g, yield 85%). The crude product may be used directly in the next step without purification. IR, MS and NMR Spectra of the product as the following:

IR (cm$^{-1}$): 2227 (w, —CN)
MS (m/z): 289.1 (M+H)$^+$
$^{13}$C NMR (CDCl$_3$): δ 136.46, 132.78, 132.38, 130.69, 130.46, 130.38, 129.90, 126.73, 124.96, 123.01, 115.09, 59.12, 49.30, 47.66, 25.47
$^1$H NMR (CDCl$_3$): δ 7.2-7.7 (4H, m), 7.0 (1H, d), 6.69 (1H, d), 5.32 (1H, s), 3.78 (1H, d), 3.65 (1H, d), 2.8-3.0 (4H, m).

(3) Preparation of (±)-(2-chlorophenyl)-(4,5,6,7-4H-thieno[3,2,-c]pyrid-5-yl) sodium acetate (V)

The mixture of (±)-(2-chlorophenyl)-(4,5,6,7-dihydro-4H-thieno[3,2,-c]pyrid-5-yl) acetonitrile (60 g, 0.208 mol), aqueous NaOH (40%, 360 g), methanol (100 mL), TEBA (1.0 g, 0.00439 mol as PTC) was stirred and refluxed in a suitable reaction flask for 12 h. After cooling and filtration, (±)-(2-chlorophenyl)-(4,5,6,7-4H-thieno[3,2,-c]pyrid-5-yl) sodium acetate (V) was obtained (61 g, 89% yield).

(4) Preparation of (±)-methyl-(2-chlorophenyl)-(4,5,6,7-4H-thieno[3,2,-c]pyrid-5-yl) acetate (I)

(±)-(2-Chlorophenyl)-(4,5,6,7-4H-thieno[3,2,-c]-pyrid-5-yl) sodium acetate (61 g, 0.185 mol), H$_2$O (250 mL) and TEBA (1.2 g, 0.00527 mol as PTC) were mixed and the pH value of the mixture was adjusted to about 10 with NaOH, 200 ml of toluene was added. Me$_2$SO$_4$ (120 g, 0.952 mol) was added dropwise at 10° C. and the reaction was stirred at room temperature for 5 h, and 40° C. for 26 h. The pH of the reaction solution was kept constantly at about 10. After the reaction was completed, the organic layer was separated and the aqueous layer was extracted with butyl acetate for several times. The combined organic layer was washed times with water and dried. After removal of solvent under reduced pressure, oily target product was obtained (32 g, 51%).

Example 9

Preparation of (±)-methyl-(2-chlorophenyl)-(4,5,6,7-4H-thieno[3,2,-c]pyrid-5-yl) acetate (I)

(1) Preparation of (±)α-Chloro-2-(2-chlorophenyl) acetonitrile

The same reaction conditions as described in step (1) for example 8 except that bromination was instead by slow purging with chlorine (80 g) for 6 h. The crude product (172 g, 92.5% yield) was distillated to afford (159 g, 85.5% yield) of qualified target product.

(2) Preparation of (±)-(2-chlorophenyl)-(4,5,6,7-4H-thieno[3,2,-c]pyrid-5-yl) acetonitrile (IV)

The same reaction conditions as described in step (2) for example 8 except that α-Chloro-2-(2-chlorophenyl)acetonitrile was used instead of α-bromo-2-(2-chlorophenyl)-acetonitrile and n-butanol as the solvent The reaction solution was cooled to 0-5° C. and filtered. The filter cake was thoroughly washed with stirring by water and cold n-butanol. Yellow fine granular solid was obtained (99.2 g, 86%) after drying. The product may be used directly for the next step without purification.

(3) Preparation of (±)-(2-chlorophenyl)-(4,5,6,7-4H-thieno[3,2,-c]pyrid-5-yl) sodium acetate (V)

The same process as described in the step (3) for example 8, while n-butanol was used as solvent and compound of formula (V) was obtained (63 g, yield 94.1%).

(4) Preparation of (±)-methyl-(2-chlorophenyl)-(4,5,6,7-4H-thieno[3,2,-c]pyrid-5-yl) acetate (I)

(±)-(2-Chlorophenyl)-(4,5,6,7-4H-thieno[3,2,-c]pyrid-5-yl) sodium acetate (63 g, 0.191 mol), H$_2$O (250 mL) and TEBA (1.2 g, 0.00526 mol as PTC) were combined and the pH value of the mixture was adjusted to about 10 with NaOH, 200 ml toluene was added. Me$_2$SO$_4$ (120 g, 0.952 mol) was added dropwise at 10° C. and the reaction was stirred at room temperature for 5 h and at 40° C. for 26 h, the pH value of the reaction mixture was kept constantly to about 10. After the reaction was completed, the organic layer was separated and the aqueous layer was extracted with butyl acetate several times. The combined organic layer was washed times with water and dried. After removal of solvent under reduced pressure, the oily target product was obtained (32 g, 51% yield).

Example 10

Preparation of (±)-methyl-(2-chlorophenyl)-(4,5,6,7-thieno[3,2,-c]pyrid-5-yl) acetate (I)

(1) Preparation of (±) α-Chloro-2-(2-chlorophenyl) acetonitrile

The same procedure as described in step (1) for example 9.

(2) Preparation of (±) α-(2-chlorophenyl)-(4,5,6,7-4H-thieno[3,2,-c]pyrid-5-yl) acetonitrile (IV)

The same reaction conditions as described in step (2) for example 8 except α-Chloro-2-(2-chlorophenyl) acetonitrile instead of α-bromo-2-(2-chlorophenyl)acetonitrile and methanol as solvent. After the reaction was completed, the reaction mixture was cooled to 0-5° C. and filtered. The filter cake was washed thoroughly by stirring with water and cold methanol. Dried and pale yellow fine granular solid was obtained (94.5 g, yield 82%). The product may be used directly in the next step without purification.

(3) Preparation of (±)-(2-chlorophenyl)-(4,5,6,7-4H-thieno[3,2,-c]pyrid-5-yl) sodium acetate (V)

The mixture of (±)-(2-chlorophenyl)-(4,5,6,7-4H-thieno-[3,2,-c]pyrid-5-yl) acetonitrile (60 g, 0.208 mol), aqueous NaOH (50%, 320 g), methanol (100 mL), TEBA (1.0 g, 0.00439 mol as PTC) was stirred and refluxed for 15 h in a suitable reaction flask. After cooling and filtration, the product of compound (V) was obtained (61 g, yield 89%).

(4) Preparation of (±)-methyl-(2-chlorophenyl)-(4,5,6,7-4H-thieno[3,2,-c]pyrid-5-yl) acetate (I)

(±)-(2-Chlorophenyl)-(4,5,6,7-4H-thieno[3,2,-c]pyrid-5-yl) sodium acetate (63 g, 0.191 mol), $H_2O$ (250 mL) and TEBA (1.2 g, 0.00527 mol as PTC) were combined and the pH value of the solution was adjusted to about 10 with NaOH. Toluene (200 ml) was then added. $Me_2SO_4$ (120 g, 0.952 mol) was added dropwise at 10° C. and the reaction was stirred at room temperature for 5 h and at 40° C. for 26 h. The pH value was kept constant to about 10. After the reaction was completed, the organic layer was separated and the aqueous layer was extracted with butyl acetate for several times. The combined organic layer was washed times with water and dried. After removal of solvent under reduced pressure, the oily target product was obtained (32 g, 51%).

Example 11

Preparation of (±)-methyl-(2-chlorophenyl)-(4,5,6,7-4H-thieno[3,2,-c]pyrid-5-yl) acetate

(1) Preparation of (±) (2-chlorophenyl)(cyano)methyl 4-methylbenzenesulfonate 2-(2-chlorophenyl)-2-hydroxyacetonitrile (16.8 g, 0.1 mol) and 4-toluene sulfonyl chloride (21 g, 0.11 mol) was dissolved in acetonitrile (80 mL) in a suitable reaction flask, and $Et_3N$ (20 g, 0.2 mol) was added to the reaction dropwise at 0-25° C. Then the solution was stirred at room temperature for 5 h and afterwards refluxed until the reaction was completed by TLC monitoring. The acetonitrile was recovered and reaction mixture was diluted by water and extracted with butyl acetate. The organic layer was washed repeatedly with water and the butyl acetate was removed under reduced pressure giving the target product (30 g, yield 93.75%).

(2) Preparation of (±)-(2-chlorophenyl)-(4,5,6,7-4H-thieno[3,2,-c]pyrid-5-yl) acetonitrile (IV)

The same reaction conditions as described in step (2) of example 8, while (±) (2-chlorophenyl)(cyano)methyl 4-methylbenzenesulfonate was used to instead of α-bromo-2-(2-chlorophenyl) acetonitrile, methanol as solvent. After the reaction was completed, the mixture was cooled to 0-5° C. and filtered. The filter cake was washed with water thoroughly, and then with cold methanol and dried. The pale yellow fine granular solid was obtained (102.5 g, yield 89%). The product may be used directly in the next step without purification.

(3) Preparation of (±)-(2-chlorophenyl)-(4,5,6,7-4H-thieno[3,2,-c]pyrid-5-yl) sodium acetate (V)

The mixture of (±)-(2-chlorophenyl)-(4,5,6,7-4H-thieno[3,2,-c]-pyrid-5-yl) acetonitrile (60 g, 0.208 mol), aqueous NaOH (35%, 360 g), methanol (100 ml), TEBA (1.0 g, 0.00439 mol as PTC) was stirred and refluxed in a suitable reaction flask for 12 h to complete the reaction. After cooling and filtration, the target product (V) was obtained (61 g, yield 89%).

(4) Preparation of (±)-methyl-(2-chlorophenyl)-(4,5,6,7-4H-thieno[3,2,-c]pyrid-5-yl) acetate (I)

The mixture of (±)-(2-chlorophenyl)-(4,5,6,7-4H-thieno [3,2,-c]pyrid-5-yl) sodium acetate (61 g, 0.156 mol), $H_2O$ (250 mL), and PEG 400 (1.5 g, 0.00527 mol as PTC) were combined and the pH value of the solution was adjusted to about 10 with $NaHCO_3$. n-butanol 200 mL was added, $Me_2SO_4$ (120 g, 0.952 mol) was added dropwise at 10° C. The reaction mixture was stirred at room temperature for 5 h and at 40° C. for 26 h with the pH value keeping to about 10. After the reaction was completed, the organic layer was separated and the aqueous layer was extracted with butyl acetate several times. The combined organic layer was washed times with water and dried. After removal of solvent under reduced pressure, oily target product was obtained (32 g, yield 51%).

Example 12

Preparation of (±)-methyl-(2-chlorophenyl)-(4,5,6,7-4H-thieno[3,2,-c]pyrid-5-yl) acetate (I)

(1) Preparation of (±) (2-chlorophenyl)(cyano)methyl 4-methylbenzenesulfonate 2-(2-chlorophenyl)-2-hydroxyacetonitrile (16.8 g, 0.1 mol) and 4-toluene sulfonyl chloride (21 g, 0.11 mol) was dissolved in toluene (100 mL) in a suitable reaction flask. Aqueous 5% NaOH (100 g, 0.125 mol) was added dropwise at 0-5° C. and the reaction continued at 10-15° C. until the reaction was completed by TLC monitoring. The organic layer was separated and the aqueous layer was extracted with toluene (50 ml×2). The combined organic layer was washed with water. After removal of toluene under reduced pressure, the target product was obtained (29 g, yield 90.6%).

(2) Preparation of (±)-(2-chlorophenyl)-(4,5,6,7-4H-thieno[3,2,-c]pyrid-5-yl) acetonitrile (IV)

The same procedure as described in step 2 for example 11.

(3) Preparation of (±)-(2-chlorophenyl)-(4,5,6,7-4H-thieno[3,2,-c]pyrid-5-yl) sodium acetate (V)

The mixture of (±)-(2-chlorophenyl)-(4,5,6,7-4H-thieno[3,2,-c]-pyrid-5-yl) acetonitrile (60 g, 0.208 mol), aqueous NaOH (45%, 360 g), methanol (100 mL), TEBA (1.0 g, 0.00439 mol as PTC) was stirred and refluxed for 14 h in a suitable reaction flask to complete the reaction. After cooling and filtration, the target product (V) was obtained (61 g, yield 89%).

(4) Preparation of (±)-methyl-(2-chlorophenyl)-(4,5,6,7-4H-thieno[3,2,-c]pyrid-5-yl) acetate (I)

The mixture of (±)-(2-chlorophenyl)-(4,5,6,7-4H-thieno[3,2,-c]pyrid-5-yl) sodium acetate (61 g, 0.156 mol), $H_2O$ (250 mL) and PEG400 (1.5 g, 0.00375 mol as PTC) were combined and the pH value of the mixture was adjusted to about 10 with $NaHCO_3$. After cooling to about 10° C., n-butanol (200 ml) was added and $Me_2SO_4$ (120 g, 0.952 mol) was added dropwise. The reaction was stirred at room temperature for 5 h and at 40° C. for 26 h with the pH value keeping to about 10. After the reaction was completed, the organic layer was separated and the aqueous layer was extracted with butyl acetate several times. The combined organic layer was washed for times with water and dried. After removal of solvent under reduced pressure, oily target product was obtained (32 g, yield 51%).

Example 13

Preparation of (±)-methyl-(2-chlorophenyl)-(4,5,6,7-4H-thieno[3,2,-c]pyrid-5-yl) acetate (I)

(1) Preparation of (±) (2-chlorophenyl)(cyano)methyl 4-methylbenzenesulfonate

The same reaction conditions as described in step (1) for example 12, while aqueous KOH (8%, 100 g, 0.14 mol) instead of aqueous NaOH and target product was obtained (29 g, 90.6% yield).

(2) Preparation of (±)-(2-chlorophenyl)-(4,5,6,7-4H-thieno[3,2,-c]pyrid-5-yl) acetonitrile (IV)

The same procedure as described in step (2) for example 12.

(3) Preparation of (±)-(2-chlorophenyl)-(4,5,6,7-4H-thieno[3,2,-c]pyrid-5-yl) sodium acetate (V)

The same procedure as described in step (3) for example 8, while n-butanol was used as solvent and the product (V) was obtained (63 g, 92% yield).

(4) Preparation of (±)-methyl-(2-chlorophenyl)-(4,5,6,7-4H-thieno[3,2,-c]pyrid-5-yl) acetate (I)

The mixture of (±)-(2-chlorophenyl)-(4,5,6,7-4H-thieno[3,2,-c]pyrid-5-yl) sodium acetate (63 g, 0.191 mol), $H_2O$ (250 mL) and PEG400 (1.5 g, 0.00375 mol as PTC) were combined and the pH value of the solution was adjusted to about 10 with $NaHCO_3$. After cooling to about 10° C., n-butanol (200 ml) was added and $Me_2SO_4$ (120 g, 0.952 mol) was added dropwise. The reaction was stirred at room temperature for 5 h and at 40° C. for 26 h with the pH keeping to about 10. After the reaction was completed, the organic layer was separated and the aqueous layer was extracted with butyl acetate for several times. The combined organic layer was washed times with water and dried. After removal of solvent under reduced pressure, oily target product was obtained (32 g, yield 51%).

Example 14

Preparation of (S)-methyl-(2-chlorophenyl)-(4,5,6,7-4H-thieno[3,2,-c]pyrid-5-yl) acetate (I)

(1) Preparation of (s) (2-chlorophenyl)(cyano)methyl 4-methylbenzenesulfonate (s)-2-(2-chlorophenyl)-2-hydroxyacetonitrile (16.8 g, 0.1 mol) and 4-toluene sulfonyl chloride (21 g, 0.11 mol) was dissolved in butyl acetate (100 mL) in a suitable reaction flask. N,N-dimethyl aniline (10 mL) was added dropwise to the mixture at 0-5° C. and the reaction continued at 20-25° C. for 3 hours, and then refluxed till the reaction was completed by TLC monitoring. Cold down the reaction mixture, 5% HCl (50 mL) was added and stirred at room temperature. Butyl acetate layer was separated and washed with water (50 ml×2). After removal of the solvent under reduced pressure, the target product was obtained (31 g, yield 96.9%).

(2) Preparation of (S)-(2-chlorophenyl)-(4,5,6,7-4H-thieno[3,2,-c]pyrid-5-yl) acetonitrile (IV)

The same procedure as described in step (2) for example 12 except (s)-2-(2-chlorophenyl)(cyano)methyl 4-methylbenzenesulfonate was used to instead of (±)-2-(2-chlorophenyl)(cyano)methyl 4-methylbenzenesulfonate, and the product was obtained (102.5 g, 89% yield, ee.>99%).

(3) Preparation of (S)-(2-chlorophenyl)-(4,5,6,7-4H-thieno[3,2,-c]pyrid-5-yl) sodium acetate (V)

The mixture of (s)-(2-chlorophenyl)-(4,5,6,7-4H-thieno[3,2,-c]-pyrid-5-yl) acetonitrile (60 g, 0.208 mol), aqueous NaOH (50%, 320 g), methanol (100 mL), 18-crown-6 (1.0 g, 0.0032 mol as PTC) was stirred and refluxed for 12 h in a suitable reaction flask until the reaction was completed. After cooling and filtration, the product was obtained (61 g, 89% yield).

(4) Preparation of (S)-methyl-(2-chlorophenyl)-(4,5,6,7-4H-thieno[3,2,-c]pyrid-5-yl) acetate (I)

The mixture of (S)-(2-chlorophenyl)-(4,5,6,7-4H-thieno[3,2,-c]pyrid-5-yl) sodium acetate (61 g, 0.156 mol), $H_2O$ (250 mL) and PEG400 (1.5 g, 0.00375 mol as PTC) were combined and the pH value of the solution was adjusted to about 10 with $NaHCO_3$. n-Butanol (200 ml) was added and cooling the mixture to about 10° C., and $Me_2SO_4$ (120 g, 0.952 mol) was added dropwise. The reaction was stirred at room temperature for 5 h and afterwards at 40° C. for 26 h with the pH keeping to about 10. After the reaction was completed, the organic layer was separated and the aqueous layer was extracted with butyl acetate for several times. The combined organic layer was washed times with water and dried. After removal of solvent under reduced pressure, the oily target product was obtained (32 g, yield 51%).

Example 15

Preparation of (±)-methyl-(2-chlorophenyl)-(4,5,6,7-4H-thieno[3,2,-c]pyrid-5-yl) acetate (I)

(1) Preparation of (±) 2-Chloro-2-(2-chlorophenyl) acetonitrile

The same procedure as described in step (1) for example 9.

(2) Preparation of (±)-(2-chlorophenyl)-(4,5,6,7-4H-thieno[3,2,-c]pyrid-5-yl) acetonitrile (IV)

The same procedure as described in step (2) for example 9.

(3) Preparation of (±)-(2-chlorophenyl)-(4,5,6,7-4H-thieno[3,2,-c]pyrid-5-yl) potassium acetate (V)

The same process as described in the step (3) for example 8, while n-butanol as solvent and aqueous KOH (40%, 360 g) as the base and the target product was obtained (70 g) and the product may be used directly for the next step without purification.

(4) Preparation of (±)-methyl-(2-chlorophenyl)-(4,5,6,7-4H-thieno[3,2,-c]pyrid-5-yl) acetate (I)

The mixture of (±)-(2-chlorophenyl)-(4,5,6,7-4H-thieno[3,2,-c]pyrid-5-yl) potassium acetate (63 g, 0.191 mol), $H_2O$ (250 mL) and PEG400 (1.5 g, 0.0375 mol as PTC) were combined and the pH value of the solution was adjusted to about 10 with $NaHCO_3$ and n-butanol (200 ml) was added. $Me_2SO_4$ (120 g, 0.952 mol) was added dropwise at about 10° C. and the reaction was stirred at room temperature for another 5 h and at 40° C. for 26 h with the pH of the reaction constantly keeping to about 10. After the reaction was completed, the organic layer was separated and the aqueous layer was extracted with butyl acetate for several times. The combined organic layer was washed with water for times and dried. After removal of solvent under reduced pressure, the oily target product was obtained (32 g, yield 51%).

Example 16

Preparation of (±)-methyl-(2-chlorophenyl)-(4,5,6,7-4H-thieno[3,2,-c]pyrid-5-yl) acetate (I)

(1) Preparation of (±) (2-chlorophenyl)(cyano)methyl methanesulfonate

The same procedures as described in step (1) for example 4, while methyl sulfonyl chloride (13 g, 0.113 mol) as esterification agent instead of 4-toluene sulfonyl chloride (21 g, 0.110 mol), and the target product was obtained (24 g, 97.6% yield).

(2) Preparation of (±)-(2-chlorophenyl)-(4,5,6,7-dihydro-4H-thieno[3,2,-c]pyrid-5-yl) acetonitrile (IV)

(±)-(2-chlorophenyl)(cyano)methyl methanesulfonate was used as the alkylation agent instead of (±)-(2-chlorophenyl)(cyano)methyl-4-methylbenzenesulfonate in methanol according to step (2) in example 11. After the reaction was finished, the reaction solution was cooled to 0-5° C. and filtered. The filter cake was washed with water and cold methanol, dried. Pale yellow fine granular solid was obtained (104.1 g, yield 90.3%). The product may be used directly in the next step without purification.

(3) Preparation of (±)-(2-chlorophenyl)-(4,5,6,7-4H-thieno[3,2,-c]pyrid-5-yl) sodium acetate (V)

The same procedure as described in step (3) for example 11, while 18-crown-6 (0.2 g, 0.00064 mol) was used as the PTC instead of TEBA and the product was obtained (62 g, 92.7% yield).

(4) Preparation of (±)-methyl-(2-chlorophenyl)-(4,5,6,7-4H-thieno[3,2,-c]pyrid-5-yl) acetate (I)

The mixture of (±)-(2-chlorophenyl)-(4,5,6,7-4H-thieno[3,2,-c]pyrid-5-yl) sodium acetate (62 g, 0.188 mol), $H_2O$ (250 mL) and PEG400 (1.5 g, 0.00375 mol as PTC) were combined and the pH value of the solution was adjusted to about 10 with $NaHCO_3$. After cooling to about 10° C., n-butanol (200 ml) was added and $Me_2SO_4$ (120 g, 0.952 mol) was added dropwise. The reaction was stirred at room temperature for 5 h and at 40° C. for 26 h with the pH value constantly keeping to about 10. After the reaction was completed, the organic layer was separated and the aqueous layer was extracted with butyl acetate several times. The combined organic layer was washed times with water and dried. After removal of solvent under reduced pressure, oily target product was obtained (32 g, yield 51%).

Example 17

Preparation of (±)-methyl-(2-chlorophenyl)-(4,5,6,7-4H-thieno[3,2,-c]pyrid-5-yl) acetate (I)

(1) Preparation of (±) (2-chlorophenyl)(cyano)methyl methanesulfonate

The same procedures as described in step (1) for example 11 while methyl sulfonyl chloride (13 g, 0.113 mol) as esterification agent instead of 4-toluene sulfonyl chloride (21 g, 0.110 mol) and target product was obtained (24 g, 97.6% yield).

(2) Preparation of (±)-(2-chlorophenyl)-(4,5,6,7-4H-thieno[3,2,-c]pyrid-5-yl) acetonitrile (IV)

The same procedure as described in step (2) for example 11.

(3) Preparation of (±)-(2-chlorophenyl)-(4,5,6,7-4H-thieno[3,2,-c]pyrid-5-yl) sodium acetate (V)

The same procedure as described in step (3) for example 9, while 18-crown-6 (0.2 g, 0.00064 mol) as the PTC instead of TEBA, and 63 g (yield, 94.1%) of compound (V) was obtained.

(4) Preparation of (±)-methyl-(2-chlorophenyl)-(4,5,6,7-4H-thieno[3,2,-c]pyrid-5-yl) acetate (I)

The mixture of (±)-(2-chlorophenyl)-(4,5,6,7-4H-thieno[3,2,-c]pyrid-5-yl) sodium acetate (63 g, 0.191 mol), $H_2O$ (250 ml) and PEG400 (1.5 g, 0.00375 mol as PTC) were combined and the pH of the solution was adjusted to about 10 with NaHCO₃. After cooling to about 10° C., n-butanol (200 ml) was added and Me₂SO₄ (120 g, 0.952 mol) was added dropwise. The reaction was stirred at room temperature for 5 h and at 40° C. for 26 h with the pH constantly keeping to about 10. After the reaction was completed, the organic layer was separated and the aqueous layer was extracted with butyl acetate several times. The combined organic layer was washed with water several times and dried. After removal of solvent under reduced pressure, the oily target product was obtained (32 g, yield 51%).

Example 18

Preparation of (R)-methyl-(2-chlorophenyl)-(4,5,6,7-4H-thieno[3,2,-c]pyrid-5-yl) acetate (XII)

(1) Preparation of (R)-(2-chlorophenyl)(cyano)methyl 4-methylbenzenesulfonate (R)-2-(2-chlorophenyl)-2-hydroxyacetonitrile (I 6.8 g, 0.1 mol) was used as the alkylation agent instead of (±)-2-(2-chlorophenyl)-2-hydroxyacetonitrile as described in step (1) for example 11 and (R)-(2-chlorophenyl)(cyano)methyl 4-methylbenzenesulfonate was obtained (31 g, ee.>99%).

(2) Preparation of (R)-(2-chlorophenyl)-(4,5,6,7-4H-thieno[3,2,-c]pyrid-5-yl) acetonitrile (IV)

(R)-(2-chlorophenyl)(cyano)methyl 4-methylbenzenesulfonate instead of α-Bromo-2-(2-chlorophenyl) acetonitrile was used as the alkylation agent in methanol as described in step (2) of example 11 after the reaction was completed. The solution was cooled to 0-5° C. and filtered. The filter cake was washed and stirred thoroughly with water and cold methanol and dried. Pale yellow fine granular solid was obtained (102.5 g, yield 89%).

(3) Preparation of (R)-(2-chlorophenyl)-(4,5,6,7-4H-thieno[3,2,-c]pyrid-5-yl) sodium acetate (V)

The same procedure as described in the step (3) for example 8, while n-butanol as solvent and product (V) was obtained (63 g, 94.1% yield).

(4) Preparation of (R)-methyl-(2-chlorophenyl)-(4,5,6,7-4H-thieno[3,2,-c]pyrid-5-yl) acetate (XII)

The mixture of (R)-(2-chlorophenyl)-(4,5,6,7-4H-thieno [3,2,-c]pyrid-5-yl) sodium acetate (63 g, 0.191 mol), H₂O (250 mL) and PEG 400 (1.5 g, as PTC) were combined and the pH value of the solution was adjusted to about 10 with NaHCO₃. After cooling to about 10° C., n-butanol (200 ml) was added and Me₂SO₄ (120 g, 0.952 mol) was added dropwise. The reaction was stirred at room temperature for 5 h and at 40° C. for 26 h with the pH constantly keeping to about 10. After the reaction was completed, the organic layer was separated and the aqueous layer was extracted with butyl acetate for several times. The combined organic layer was washed times with water and dried. After removal of solvent under reduced pressure, oily target product was obtained (32 g, yield 51%).

Example 19

Preparation of (S)-methyl-(2-chlorophenyl)-(4,5,6,7-4H-thieno[3,2,-c]pyrid-5-yl) acetate (XII)

(1) Preparation of (S)-(2-chlorophenyl)(cyano)methyl 4-methylbenzenesulfonate (S)-2-(2-chlorophenyl)-2-hydroxyacetonitrile (16.8 g, 0.1 mol) was used as the alkylation agent instead of α-bromo-2-(2-chlorophenyl) acetonitrile as described in step (1) for example 11 and the target product (S)-(2-chlorophenyl)(cyano)methyl 4-methylbenzenesulfonate was obtained (23 g, 86% yield, ee.>99%)

(2) Preparation of (S)-(2-chlorophenyl)-(4,5,6,7-4H-thieno[3,2,-c]pyrid-5-yl) acetonitrile (IV)

(S)-(2-chlorophenyl)(cyano)methyl 4-methylbenzenesulfonate instead of (±) (2-chlorophenyl)(cyano)methyl 4-methylbenzenesulfonate was used as the alkylation agent in methanol as described in step 2 for example 11.

(3) Preparation of (S)-(2-chlorophenyl)-(4,5,6,7-4H-thieno[3,2,-c]pyrid-5-yl) sodium acetate (V)

After the reaction was completed as described in the above step (2), the solution was cooled to room temperature, aqueous NaOH (35%, 600 g) and TEBA (1.5 g, 0.00659 mol as PTC) were added. The solution was stirred and refluxed for 12 h in a suitable reaction flask. After cooling and filtration, the product of compound (V) was obtained (108 g).

(4) Preparation of (S)-methyl-(2-chlorophenyl)-(4,5,6,7-4H-thieno[3,2,-c]pyrid-5-yl) acetate (XII)

The mixture of (S)-(2-chlorophenyl)-(4,5,6,7-4H-thieno [3,2,-c]pyrid-5-yl) sodium acetate (63 g, 0.191 mol), H₂O (250 mL) and PEG 400 (1.5 g, 0.00375 mol as PTC) were combined and the pH of the solution was adjusted at about 10 with NaHCO₃. n-Butanol (200 ml) was added. After cooling the mixture to about 10° C. Me₂SO₄ (120 g, 0.952 mol) was added dropwise. The reaction was stirred at room temperature for 5 h and afterwards at 40° C. for 26 h with the pH value constantly keeping to about 10. After the reaction was completed, the organic layer was separated and the aqueous layer was extracted with butyl acetate several times. The combined organic layer was washed times with water and dried. After removal of solvent under reduced pressure, the oily target product was obtained (32 g, yield 51%).

Example 20

Preparation of (S)-methyl-(2-chlorophenyl)-(4,5,6,7-4H-thieno[3,2,-c]pyrid-5-yl) acetate (XII)

The mixture of (S)-(2-chlorophenyl)-(4,5,6,7-4H-thieno [3,2,-c]-pyrid-5-yl) acetonitrile (64 g, 0.252 mol), TEBA (1.0 g, 0.00439 mol as PTC), aqueous KOH (35%, 360 g), n-butanol (100 mL) was stirred and refluxed in a suitable reaction flask for 10 h. After cooling and filtration, 64 g product of (s)-methyl-(2-chlorophenyl)-(4,5,6,7-4H-thieno[3,2,-c]pyrid-5-yl) potassium acetate was obtained with 74% yield, The mixture of (s)-(2-chlorophenyl)-(4,5,6,7-4H-thieno[3, 2,-c]pyrid-5-yl) potassium acetate (63 g, 0.183 mol), H₂O (250 mL) and PEG400 (1.5 g, 0.00375 mol as PTC) were combined and the pH value of the solution was adjusted to about 10 with NaHCO₃. n-Butanol (200 ml) was added. After cooling to about 10° C., Me₂SO₄ (120 g, 0.952 mol) was added dropwise. The reaction was stirred at room temperature for 5 h and at 40° C. for 26 h with the pH value constantly keeping to about 10. After the reaction was completed, the organic layer was separated and the aqueous layer was extracted with butyl acetate several times. The combined organic layer was washed times with water and dried. After removal of solvent under reduced pressure, oily target product was obtained (32 g, yield 51%).

Example 21

Preparation of (±)-methyl-(2-chlorophenyl)-(4,5,6,7-4H-thieno[3,2,-c]pyrid-5-yl) acetate (I)

The mixture of (±)-methyl-(2-chlorophenyl)-(4,5,6,7-4H-thieno[3,2,-c]-pyrid-5-yl) acetamide (61 g, 0.199 mol), TEBA (1.0 g, 0.00439 mol as PTC), aqueous NaOH (50%, 320 g), methanol (100 mL) was stirred and refluxed in a suitable reaction flask for 18 h. After cooling and filtration, 61 g of (±)-methyl-(2-chlorophenyl)-(4,5,6,7-4H-thieno[3,2,-c]pyrid-5-yl) sodium acetate was obtained in 93% yield.

The mixture of so obtained (±)-(2-chlorophenyl)-(4,5,6,7-4H-thieno[3,2,-c]pyrid-5-yl) sodium acetate (61 g, 0.195 mol), $H_2O$ (250 mL) and TEBA (1.2 g, 0.00527 mol as PTC) were combined and the pH value of the solution was adjusted to about 10 with NaOH. Toluene (200 ml) was added. After cooling to about 10° C. $Me_2SO_4$ (120 g, 0.952 mol) was added dropwise. The reaction was carried out at room temperature for 5 h and at 40° C. for 26 h with the pH value constantly keeping to about 10. After the reaction was completed, the organic layer was separated and the aqueous layer was extracted with butyl acetate several times. The combined organic layer was washed times with water and dried. After removal of solvent under reduced pressure, oily target product was obtained (32 g, yield 51%).

The following are resolution examples of racemic Clopidogrel of this invention:

Example 22

Preparation of (s)-Clopidogrel (−)-camphor sulfonate

Racemic Clopodigrel (33 g 0.103 mol) is dissolved in toluene (150 mL) and R-camphor sulfonate nonohydrate (15 g, 0.06 mol) is added batchwise, the reaction system released small amount of heat. The mixture is stirred at room temperature for 5 h, and some crystal seed of (s)-Clopidogrel (−)-camphor sulfonate is added, stirring is continued to precipitate the enantiomer thoroughly to reach kinetic balance. After additional stirring for 48 h at room temperature, the precipitate is filtered, and washed with small amount of toluene to give the target solid product (24.8 g, yield 88.6%, ee 95.1%). The crude product is refluxed in isopropanol (1:1 W/V) and cooled to room temperature. The qualified (s)-Clopidogrel (−)-camphor sulfonate (18.8 g, yield 75.8%, ee 99.1%) is obtained after filtration, drying and general workup.

Example 23

Preparation of (s)-Clopidogrel (−)-camphor sulfonate

Racemic clopodigrel (33 g, 0.102 mol) is dissolved in toluene (130 mL) and R-camphor sulfonate nonohydrate (13.2 g, 0.0528 mol) is added batchwise the reaction system released small amount of heat. The mixture is stirred at 50° C. for 3 h, and cooled to room temperature. Some crystal seed of (s)-Clopidogrel (−)-camphor sulfonate is added, stirring was continued to precipitate the enantiomer thoroughly to reach kinetic balance. After additional stirring for 48 h at room temperature, the precipitate is filtered, and washed with small amount of toluene to give the target solid product (23.8 g, yield 84.7%, ee 97.5%). The crude product is refluxed and washed in isopropanol (solid to isopropanol 1:1 w/v) and cooled to room temperature. The qualified (s)-Clopidogrel (−)-camphor sulfonate (19.7 g, yield 82.8%, ee 99.5%) is obtained after filtration, drying and general workup.

Example 24

Preparation of (s)-Clopidogrel (−)-camphor sulfonate

Racemic clopodigrel (33 g, 0.102 mol) is dissolved in toluene (130 mL) and R-camphor sulfonate nonohydrate (10.2 g, 0.040 mol) is added batchwise the reaction system released small amount of heat. The mixture is stirred at room temperature for 5 h, and cooled to room temperature. Some crystal seed of (s)-Clopidogrel (−)-camphor sulfonate is added, stirring was continued to precipitate the enantiomer thoroughly to reach kinetic balance. After additional stirring for 48 h at room temperature, the precipitate is filtered, and washed with small amount of toluene to give the target solid product (22.6 g, yield 79.6%, ee 98.5%). The crude product is refluxed and washed in butyl acetate (solid to butyl acetate 1:1 w/v) and cooled to room temperature. The qualified (s)-Clopidogrel (−)-camphor sulfonate (18.9 g, yield 83.6%, ee 99.4%) is obtained after filtration, drying and general workup.

Example 25

Preparation of (s)-Clopidogrel (−)-camphor sulfonate

Racemic clopodigrel (33 g, 0.102 mol) is dissolved in isopropanol (130 mL) and R-camphor sulfonate nonohydrate (13.2 g, 0.053 mol) is added batchwise, the reaction system released small amount of heat. The mixture is stirred at 35° C. for 5 h, and cooled to room temperature. Some crystal seed of (s)-Clopidogrel (−)-camphor sulfonate is added, stirring was continued to precipitate the enantiomer thoroughly to reach kinetic balance. After additional stirring for 48 h at room temperature, the precipitate is filtered, and washed with small amount of propanol to give the target solid product (24 g, yield 85.4%, ee 97.5%). The crude product is refluxed and washed in isopropanol (solid to isopropanol 1:1 w/v) and cooled to room temperature. The qualified (s)-Clopidogrel (−)-camphor sulfonate (19.9 g, yield 82.9%, ee 99.5%) is obtained after filtration, drying and general workup.

Example 26

Preparation of (s)-Clopidogrel (−)-camphor sulfonate

Racemic clopodigrel (33 g, 0.102 mol) is dissolved in isopropanol (130 mL) and R-camphor sulfonate nonohydrate (12.7 g, 0.0495 mol) is added batchwise, the reaction system released small amount of heat. The mixture is stirred at room temperature for 5 h and cooled to room temperature. Some crystal seed of (s)-Clopidogrel (−)-camphor sulfonate is added, stirring was continued to precipitate the enantiomer thoroughly to reach kinetic balance. After additional stirring for 48 h at room temperature, the precipitate is filtered, and washed with small amount of propanol to give the target solid product (23.4 g, yield 83.3%, ee 98%). The crude product is refluxed and washed in isopropanol (solid to isopropanol 1:1 w/v) and cooled to room temperature (15° C. to 25° C.). The qualified (s)-Clopidogrel (−)-camphor sulfonate (19.5 g, yield 83.3%, ee 99.3%) is obtained after filtration, drying and general workup.

Example 27

Preparation of (s)-Clopidogrel (−)-camphor sulfonate

Racemic clopodigrel (33 g, 0.102 mol) is dissolved in xylene (130 mL) and R-camphor sulfonate nonohydrate (13.2 g, 0.0495 mol) is added batchwise, the reaction system released small amount of heat. The mixture is stirred at room temperature for 5 h. Some crystal seed of (s)-Clopidogrel (−)-camphor sulfonate is added, stirring was continued to precipitate the enantiomer thoroughly to reach kinetic balance. After additional stirring for 48 h at room temperature, the precipitate is filtered, and washed with small amount of xylene to give the target solid product (23.6 g, yield 84%, ee 97.5%). The crude product is refluxed and washed in butyl acetate (solid to butyl acetate 1:1 w/v) and cooled to room temperature (15° C. to 25° C.). The qualified (s)-Clopidogrel (−)-camphor sulfonate (19.2 g, yield 81.3%, ee 99.4%) is obtained after filtration, drying and general workup

Example 28

Preparation of (s)-Clopidogrel (−)-camphor sulfonate

Racemic clopodigrel (33 g, 0.102 mol) is dissolved in xylene (130 mL) and R-camphor sulfonate nonohydrate (10.2 g, 0.040 mol) is added batchwise, the reaction system released small amount of heat. The mixture is stirred at 40° C. for 5 h and cooled to room temperature. Some crystal seed of (s)-Clopidogrel (−)-camphor sulfonate is added, stirring was continued to precipitate the enantiomer thoroughly to reach kinetic balance. After additional stirring for 48 h at room temperature, the precipitate is filtered, and washed with small amount of xylene to give the target solid product (22.6 g, yield 78%, ee 98.5%). The crude product is refluxed and washed in isopropanol (solid to isopropanol 1:1 w/v) and cooled to room temperature (15° C. to 25° C.). The qualified (s)-Clopidogrel (−)-camphor sulfonate (19.5 g, yield 86.3%, ee 99.3%) is obtained after filtration, drying and general workup

Example 29

Preparation of (s)-Clopidogrel (−)-camphor sulfonate

Racemic clopodigrel (33 g, 0.102 mol) is dissolved in chlorobenzene (130 mL) and R-camphor sulfonate nonohydrate (13.2 g, 0.04 mol) is added batchwise, the reaction system released small amount of heat. The reaction mixture is stirred at 60° C. for 5 h and cooled to room temperature. Some crystal seed of (s)-Clopidogrel (−)-camphor sulfonate is added, stirring was continued to precipitate the enantiomer thoroughly to reach kinetic balance. After additional stirring for 48 h at room temperature, the precipitate is filtered, and washed with small amount of chlorobenzene to give the target solid product (23.4 g, yield 83.3%, ee 97.5%). The crude product is refluxed and washed in isopropanol (solid to isopropanol 1:1 w/v) and cooled to room temperature (15° C. to 25° C.). The qualified (s)-Clopidogrel (−)-camphor sulfonate (19.4 g, yield 82.9%, ee 99.4%) is obtained after filtration, drying and general workup

Example 30

Preparation of (s)-Clopidogrel (−)-camphor sulfonate

Racemic clopodigrel (33 g, 0.102 mol) is dissolved in ethyl acetate (150 mL) and R-camphor sulfonate nonohydrate (13.2 g, 0.04 mol) is added batchwise, the reaction system released small amount of heat. The reaction mixture is stirred at room temperature for 5 h. Some crystal seed of (s)-Clopidogrel (−)-camphor sulfonate is added, stirring was continued to precipitate the enantiomer thoroughly to reach kinetic balance. After additional stirring for 48 h at room temperature, the precipitate is filtered, and washed with small amount of ethyl acetate to give the target solid product (24 g, yield 85.4%, ee 97.8%). The crude product is refluxed and washed in butyl acetate (solid to butyl acetate 1:1 w/v) and cooled to room temperature. The qualified (s)-Clopidogrel (−)-camphor sulfonate (20.1 g, yield 83.8%, ee 99.5%) is obtained after filtration, drying and general workup

Example 31

(s)-Preparation of Clopidogrel (−)-camphor sulfonate

Racemic clopodigrel (33 g, 0.102 mol) is dissolved in 1,2-dichloroethane (130 mL) and R-camphor sulfonate nonohydrate (13.2 g, 0.04 mol) is added batchwise, the reaction system released small amount of heat. The reaction mixture is stirred at room temperature for 5 h. Some crystal seed of (s)-Clopidogrel (−)-camphor sulfonate is added, stirring was continued to precipitate the enantiomer thoroughly to reach kinetic balance. After additional stirring for 48 h at room temperature, the precipitate is filtered, and washed with small amount of 1,2-dichloroethane to give the target solid product (23.5 g, yield 83.6%, ee 97.8%). The crude product is refluxed and washed in isopropanol (solid to isopropanol 1:1 w/v) and cooled to room temperature. The qualified (s)-Clopidogrel (−)-camphor sulfonate (19.9 g, yield 84.7%, ee 99.4%) is obtained after filtration, drying and general workup

Example 32

Preparation of (s)-Clopidogrel bisulfate salt (S)-Clopidogrel (−)-camphor sulfonate (26 g, 0.047 mol) is dissolved in anhydrous acetone (100 mL) and anhydrous NaHCO$_3$ (5 g, 0.060 mol) is added to the solution. The mixture is refluxed for more than 6 h to form sodium salt of camphor sulfonic acid completely and gradually cooled to −10° C. and filtered. The solid was washed with minimal acetone and the insoluble (s)-Clopidogrel (−)-camphor sodium sulfonate was recovered. The solution of (s)-Clopidogrel free base in acetone was added with equal molar of concentrated H$_2$SO$_4$ and the white solid is formed in half an hour. After filtration and drying, 18.1 g of (s)-Clopidogrel bisulfate salt is obtained (yield 92%, ee 99.2%).

Example 33

Preparation of (s)-Clopidogrel bisulfate salt (S)-Clopidogrel (−)-camphor sulfonate (26 g, 0.047 mol) is dissolved in anhydrous acetone (100 mL) and anhydrous NaOAc (5 g, 0.061 mol) is added to the solution. The mixture is refluxed for more than 6 h to form sodium salt of camphor sulfonic acid completely and gradually cooled to −10° C. and filtered. The solid was washed with minimal amount of acetone and the insoluble (s)-Clopidogrel (−)-camphor sodium sulfonate was recovered. The solution of (s)-Clopidogrel free base in acetone was added with equal molar of concentrated H$_2$SO$_4$ and the white solid is formed in half an hour. After filtration and drying, 17.7 g of (s)-Clopidogrel bisulfate salt is obtained (yield 90%, ee 99.4%).

Example 34

Preparation of (s)-Clopidogrel bisulfate salt (S)-Clopidogrel (−)-camphor sulfonate (26 g, 0.047 mol) is dissolved in anhydrous butanone (120 mL) and anhydrous KOAc (6 g,) is added to the solution. The mixture is refluxed for more than 6 h to form potassium salt of camphor sulfonic acid completely and gradually cooled to −10° C. and filtered. The solid was washed with minimal amount of butanone, and the insoluble (s)-Clopidogrel (−)-camphor sodium sulfonate was recovered. The solution of (s)-Clopidogrel free base in acetone was added with equal molar of concentrated $H_2SO_4$ and the white solid is formed in half an hour. After filtration and drying, 17.7 g of target product is obtained (yield 90%, ee 99.1%).

Example 35

Preparation of (s)-Clopidogrel hydrobromide (S)-Clopidogrel (−)-camphor sulfonate (26 g, 0.047 mol) is dissolved in ethyl acetate (100 mL) and $NEt_3$ (6 g, 0.059 mol) is added to the solution. The mixture is refluxed for more than 6 h to form triethylamine salt of camphor sulfonic acid completely and gradually cooled to −10° C. and filtered. The solid is washed with a little amount of ethyl acetate and the insoluble (s)-Clopidogrel (−)-camphor sulfonic acid triethylamine salt is recovered. The solution of (s)-Clopidogrel free base in ethyl acetate is added with equal molar HBr and the white solid is formed in half an hour. After filtration and drying, 16.1 g of target product is obtained (yield 85%, ee 99.2%).

Example 36

Preparation of (s)-Clopidogrel hydrobromide (S)-Clopidogrel (−)-camphor sulfonate (26 g, 0.047 mol) is dissolved in toluene (120 mL) and anhydrous $NaHCO_3$ (5 g, 0.060 mol) is added to the solution. The mixture is refluxed for more than 6 h to form sodium salt of camphor sulfonic acid completely and gradually cooled to −10° C. and filtered. The solid is washed with a little amount of toluene and the insoluble (s)-Clopidogrel (−)-camphor sulfonic acid sodium salt is recovered. The solution of (s)-Clopidogrel free base in toluene is added with equal molar HBr and the white solid is formed in half an hour. After filtration and drying, 17.2 g of target product is obtained (yield 91%, ee 99.2%).

Example 37

Preparation of (s)-Clopidogrel hydrochloride (S)-Clopidogrel (−)-camphor sulfonate (26 g, 0.047 mol) is dissolved in methanol (100 mL) and sodium methoxide (2.8 g, 0.052 mol) is added to the solution. The mixture is refluxed for more than 6 h to form sodium salt of camphor sulfonic acid completely and gradually cooled to −10° C. and filtered. The solid is washed with a little amount of methanol and the insoluble (s)-Clopidogrel (−)-camphor sulfonic acid sodium salt is recovered. The solution of (s)-Clopidogrel free base in methanol is added with equal molar HCl and the white solid is formed in half an hour. After filtration and drying, 15.1 g of target product is obtained (yield 90%, ee 99.4%,).

Example 38

Preparation of (s)-Clopidogrel hydrochloride (S)-Clopidogrel (−)-camphor sulfonate (26 g, 0.047 mol) is dissolved in ethanol (150 mL) and anhydrous $KHCO_3$ (6 g, 0.061 mol) is added to the solution. The mixture is refluxed for more than 6 h to form potassium salt of camphor sulfonic acid completely and gradually cooled to −10° C. and filtered. The solid is washed with a little amount of ethanol and the insoluble (s)-Clopidogrel (−)-camphor sulfonic acid potassium salt is recovered. The solution of (s)-Clopidogrel free base in ethanol is added with equal molar HCl and the white solid is formed in half an hour. After filtration and drying, 15.7 g of target product is obtained (yield 93%, ee 99.4%).

The following are racemic resolution comparative examples using the present techniques:

Comparative Example 1

Preparation of (s)-Clopidogrel (−)-camphor sulfonate

Racemic clopodigrel (33 g, 0.102 mol) is dissolved in toluene (200 mL) and (R)-camphor sulfonate monohydrate (15 g, 0.06 mol) is dissolved in DMF (20 mL). The solution of toluene is added to the solution of DMF at 30° C. The mixture is kept at 30° C. and a crystal seed of (s)-Clopidogrel (−)-camphor sulfonate is added, and then cooled to 15° C. wherein the solid is precipitated. Optical rotation of the solution is detected every 30 minutes and the reaction is stopped when the optical rotation do not decreased. The mixture is filtered and the solid is washed with a little quantity of toluene. After drying, (s)-Clopidogrel (−)-camphor sulfonate is obtained in only 80.6% ee (13.4 g, yield 47.8%).

Comparative Example 2

(S)-Clopidogrel (−)-camphor sulfonate

Racemic clopodigrel (33 g, 0.102 mol) is dissolved in acetone (200 mL) and refluxed for 15 minutes. (R)-camphor sulfonate monohydrate (25.6 g, 0.102 mol) in water (15 mL) is added to the mixture and the reaction is refluxed for more than 10 h. The solution is cooled to room temperature, and then to 0-5° C., no solid is precipitated out Above two comparative examples showed that the method of this invention is better than present technique. Both the purity of resolution product and its yield are high.

The following examples are the racemization examples of the preparation of (R)-methyl-(2-chlorophenyl)-(6,7-4H-thieno-[3,2,-c]pyrid-5-yl) acetate Example 39

Synthesis of (±)-(2-chlorophenyl)-(4,5,6,7-4H-thieno [3,2,-c]pyrid-5-yl) sodium acetate (V)

The mixture of (R)-methyl-(2-chlorophenyl)-(4,5,6,7-4H-thieno-[3,2,-c]pyrid-5-yl) acetate (60 g, 0.187 mol), aqueous NaOH (50%, 360 g), n-butanol (100 mL), TEBA (1.0 g, 0.00439 mol as PTC) was refluxed for 12 hours in a suitable reaction flask. After cooling to room temperature, the suspension was filtered and the target product was obtained in ee=0% (60 g, yield 97.9%).

Example 40

Synthesis of (±)-(2-chlorophenyl)-(4,5,6,7-4H-thieno[3,2,-c]pyrid-5-yl) potassium acetate (V)

The mixture of (R)-methyl-(2-chlorophenyl)-(4,5,6,7-4H-thieno[3,2,-c]-pyrid-5-yl) acetate (60 g, 0.187 mol), aqueous KOH (50%, 360 g), methanol (100 mL), TEBA (1.0 g, 0.00439 mol as PTC) was refluxed for 12 hours in a suitable reaction flask. After cooling to room temperature, the suspension was filtered and the target product was obtained in ee=0% (62.5 g, yield 97.2%,).

Example 41

Synthesis of (±)-(2-chlorophenyl)-(4,5,6,7-4H-thieno[3,2,-c]pyrid-5-yl) sodium acetate (V)

The mixture of (R)-methyl-(2-chlorophenyl)-(4,5,6,7-4H-thieno-[3,2,-c]pyrid-5-yl) acetate (60 g, 0.187 mol), aqueous NaOH (40%, 360 g), n-butanol (100 mL), PEG400 (1.5 g, 0.00375 mol as PTC) was refluxed for 15 hours in a suitable reaction flask. After cooling to room temperature, the suspension was filtered and the target product was obtained in ee=0% (59 g, yield 96.2%).

Example 42

Synthesis of (±)-(2-chlorophenyl)-(4,5,6,7-4H-thieno[3,2,-c]pyrid-5-yl) sodium acetate (V)

The mixture of (R)-methyl-(2-chlorophenyl)-(4,5,6,7-4H-thieno-[3,2,-c]pyrid-5-yl) acetate (60 g, 0.187 mol), aqueous NaOH (40%, 360 g), n-butanol (100 mL) was refluxed for 16 hours in a suitable reaction flask. After cooling to room temperature, the suspension was filtered and the target product was obtained in ee=0% (59 g, yield 96.2%).

Example 43

Synthesis of (±)-(2-chlorophenyl)-(4,5,6,7-4H-thieno[3,2,-c]pyrid-5-yl) potassium acetate (V)

The mixture of (R)-methyl-(2-chlorophenyl)-(4,5,6,7-4H-thieno-[3,2,-c]pyrid-5-yl) acetate (60 g, 0.187 mol), aqueous KOH (35%, 360 g), ethanol (100 mL) was refluxed for 18 hours in a suitable reaction flask. After cooling to room temperature, the suspension was filtered and the target product was obtained in ee=0% (60.5 g, yield 94.1%).

Example 44

Synthesis of (±)-(2-chlorophenyl)-(4,5,6,7-4H-thieno[3,2,-c]pyrid-5-yl) sodium acetate (V)

The mixture of (R)-methyl-(2-chlorophenyl)-(4,5,6,7-4H-thieno-[3,2,-c]pyrid-5-yl) acetate (60 g, 0.187 mol), aqueous NaOH (35%, 360 g), 18-crown-6 (0.2 g, 0.00064 mol as PTC) was refluxed for 18 hours in a suitable reaction flask. After cooling to room temperature, the suspension was filtered and the target product was obtained in ee=0% (58 g, yield 94.6%).

Example 45

Synthesis of (±)-(2-chlorophenyl)-(4,5,6,7-4H-thieno[3,2,-c]pyrid-5-yl) sodium acetate (V)

The mixture of (R)-methyl-(2-chlorophenyl)-(4,5,6,7-4H-thieno-[3,2,-c]pyrid-5-yl) acetate (60 g, 0.187 mol), aqueous NaOH (20%, 360 g), methanol (100 mL), PEG 400 (1.5 g, 0.00375 mol as PTC) was refluxed for 20 hours in a suitable reaction flask. After cooling to room temperature, the suspension was filtered and the target product was obtained in ee=0% (56 g, yield 91.4%).

Example 46

Synthesis of (±)-(2-chlorophenyl)-(4,5,6,7-4H-thieno[3,2,-c]pyrid-5-yl) sodium acetate (V)

The mixture of (R)-methyl-(2-chlorophenyl)-(4,5,6,7-4H-thieno-[3,2,-c]pyrid-5-yl) acetate (60 g, 0.187 mol), aqueous NaOH (6%, 360 g), ethanol (100 mL), TEBA (1.0 g, 0.00439 mol as PTC) was refluxed for 20 hours in a suitable reaction flask. After cooling to room temperature, the suspension was filtered and the target product was obtained in ee=5% (55 g, yield 89.7%).

Example 47

Synthesis of (±)-(2-chlorophenyl)-(4,5,6,7-4H-thieno[3,2,-c]pyrid-5-yl) sodium acetate (V)

The mixture of (R)-methyl-(2-chlorophenyl)-(4,5,6,7-4H-thieno-[3,2,-c]pyrid-5-yl) acetate (60 g, 0.187 mol), aqueous NaOH (15%, 360 g) was refluxed for 15 hours in a suitable reaction flask. After cooling to room temperature, the suspension was filtered and the target product was obtained in ee=0% (58 g, yield 94.6%).

Example 48

Synthesis of (±)-(2-chlorophenyl)-(4,5,6,7-4H-thieno[3,2,-c]pyrid-5-yl) sodium acetate (V)

The mixture of (R)-methyl-(2-chlorophenyl)-(4,5,6,7-4H-thieno-[3,2,-c]pyrid-5-yl) acetate (60 g, 0.187 mol), $Na_2CO_3$ (80 g, 0.755 mol), water (200 mL), ethanol (100 mL), TEBA (1.0 g, 0.00439 mol as PTC) was refluxed for 15 hours in a suitable reaction flask. After cooling to room temperature, the suspension was filtered and the target product was obtained in ee=0% (56 g, yield 91.4%).

Example 49

Synthesis of (±)-(2-chlorophenyl)-(4,5,6,7-4H-thieno[3,2,-c]pyrid-5-yl) potassium acetate (V)

The mixture of (R)-methyl-(2-chlorophenyl)-(4,5,6,7-4H-thieno-[3,2,-c]pyrid-5-yl) acetate (60 g, 0.187 mol), $K_2CO_3$ (100 g, 0.579 mol), water (300 mL) was refluxed for 15 hours in a suitable reaction flask. After cooling to room temperature, the suspension was filtered and the target product was obtained in ee=0% (60 g, yield 93%).

Example 50

Synthesis of (±)-(2-chlorophenyl)-(4,5,6,7-4H-thieno[3,2,-c]pyrid-5-yl) sodium acetate (V)

The mixture of (R)-methyl-(2-chlorophenyl)-(4,5,6,7-4H-thieno-[3,2,-c]pyrid-5-yl) acetate (60 g, 0.187 mol), $NaHCO_3$ (80 g, 0.952 mol), water (200 mL), ethanol (100 mL), PEG400 (1.5 g, 0.00375 mol as PTC) was refluxed for 18 hours in a suitable reaction flask. After cooling to room temperature, the suspension was filtered and the target product was obtained in ee=5% (55 g, yield 89.7%).

Example 51

Synthesis of (±)-(2-chlorophenyl)-(4,5,6,7-4H-thieno [3,2,-c]pyrid-5-yl) sodium acetate (V)

The mixture of (R)-methyl-(2-chlorophenyl)-(4,5,6,7-4H-thieno-[3,2,-c]pyrid-5-yl) acetate (60 g, 0.187 mol), aqueous NaOH (10%, 360 g), ethanol (100 mL), TEBA (1.0 g, 0.00439 mol as PTC) was put into the reaction kettle and heated to 130° C. under 2 atm pressure for 8 hours. After cooling to room temperature, the suspension was filtered and the target product was obtained in ee=0% (57.5 g, yield 93.8%).

Example 52

Synthesis of (±)-(2-chlorophenyl)-(4,5,6,7-4H-thieno [3,2,-c]pyrid-5-yl) sodium acetate (V)

The same procedure as described in the example 39, while (S)-methyl-(2-chlorophenyl)-(4,5,6,7-4H-thieno[3,2,-c]pyrid-5-yl) acetate was used instead of (R)-methyl-(2-chlorophenyl)-(4,5,6,7-4H-thieno[3,2,-c]pyrid-5-yl) acetate and the target product was obtained in ee=0% (59 g, yield 96.2%).

Example 53

Synthesis of (±)-(2-chlorophenyl)-(4,5,6,7-4H-thieno [3,2,-c]pyrid-5-yl) sodium acetate (V)

The same procedure as described for example 41, while (S)-methyl-(2-chlorophenyl)-(4,5,6,7-4H-thieno[3,2,-c]pyrid-5-yl) acetate was used instead of (R)-methyl-(2-chlorophenyl)-(4,5,6,7-dihydro-4H-thieno[3,2,-c]pyrid-5-yl) acetate and the target product was obtained in ee=0% (58 g, yield 94.6%).

Example 54

Synthesis of (±)-(2-chlorophenyl)-(4,5,6,7-4H-thieno [3,2,-c]pyrid-5-yl) sodium acetate (V)

The same procedure as described for example 39, while (S)-methyl-(2-chlorophenyl)-(4,5,6,7-4H-thieno[3,2,-c]pyrid-5-yl) acetate (ee=64%) was used instead of (R)-methyl-(2-chlorophenyl)-(4,5,6,7-4H-thieno[3,2,-c]pyrid-5-yl) acetate and the target product was obtained in ee=0% (59 g, yield 96.2%).

Example 55

Synthesis of (±)-(2-chlorophenyl)-(4,5,6,7-4H-thieno [3,2,-c]pyrid-5-yl) sodium acetate (V)

The same procedure as described for example 39, while (S)-methyl-(2-chlorophenyl)-(4,5,6,7-4H-thieno[3,2,-c]pyrid-5-yl) acetate (ee=43%) was used instead of (R)-methyl-(2-chlorophenyl)-(4,5,6,7-4H-thieno[3,2,-c]pyrid-5-yl) acetate and the target product was obtained in ee=0% (55 g, yield 89.7%).

Example 56

Synthesis of (±)-(2-chlorophenyl)-(4,5,6,7-4H-thieno [3,2,-c]pyrid-5-yl) sodium acetate (V)

The mixture of (R)-(2-chlorophenyl)-(4,5,6,7-4H-thieno [3,2,-c]pyrid-5-yl) acetonitrile (60 g, 0.236 mol), aqueous NaOH (40%, 360 g), methanol (100 mL), TEBA (1.0 g, 0.00439 mol as PTC) was refluxed for more than 12 hours in a suitable reaction flask. The reacted solution may be used directly in the next step or cooled and filtered to obtain the target compound (V) in ee=0% (61 g, yield 89.1%).

Example 57

Synthesis of (±)-(2-chlorophenyl)-(4,5,6,7-4H-thieno [3,2,-c]pyrid-5-yl) sodium acetate (V)

The same procedure as described for example 39, while ethanol as solvent and PEG 400 (1.5 g, 0.00375 mol) as the PTC and the target product was obtained in ee=0% (63 g, yield 92%).

Example 58

Synthesis of (±)-(2-chlorophenyl)-(4,5,6,7-4H-thieno [3,2,-c]pyrid-5-yl) sodium acetate (V)

The mixture of (R)-(2-chlorophenyl)-(4,5,6,7-4H-thieno [3,2,-c]pyrid-5-yl) acetonitrile (60 g, 0.236 mol), aqueous NaOH (50%, 360 g), ethanol (100 mL), PEG 600 (1.5 g, 0.00375 mol as PTC) was refluxed for more than 12 hours in a suitable reaction flask. The reacted solution may be used directly in the next step or cooled and filtered to obtain the target product (63.5 g, yield 92.7%, ee=0%).

Example 59

Synthesis of (±)-(2-chlorophenyl)-(4,5,6,7-4H-thieno [3,2,-c]pyrid-5-yl) potassium acetate The mixture of (R)-(2-chlorophenyl)-(4,5,6,7-4H-thieno [3,2,-c]pyrid-5-yl) acetonitrile (60 g, 0.236 mol), aqueous KOH (50%, 360 g), ethanol (100 mL), TEBA (1.0 g, 0.00439 mol as PTC) was refluxed for more than 12 hours in a suitable reaction flask. The reacted solution may be used directly in the next step or cooled and filtered to obtain the target product (69 g, yield 96.4%, ee=0%).

Example 60

Synthesis of (±)-(2-chlorophenyl)-(4,5,6,7-4H-thieno [3,2,-c]pyrid-5-yl) sodium acetate (V)

The mixture of (S)-(2-chlorophenyl)-(4,5,6,7-4H-thieno [3,2,-c]pyrid-5-yl) acetonitrile (60 g, 0.236 mol), aqueous NaOH (50%, 360 g), methanol (100 mL), 18-crown-6 (0.2 g, 0.00064 mol as PTC) was refluxed for more than 12 hours in a suitable reaction flask. The reacted solution may be used directly in the next step or cooled and filtered to obtain the target product in ee=0% (64 g, yield 93.4%).

Example 61

Synthesis of (±)-(2-chlorophenyl)-(4,5,6,7-4H-thieno [3,2,-c]pyrid-5-yl) potassium acetate (V)

The mixture of (S)-(2-chlorophenyl)-(4,5,6,7-4H-thieno [3,2,-c]pyrid-5-yl) acetonitrile (60 g, 0.236 mol), aqueous KOH (40%, 360 g), n-butanol (100 mL), TEBA (1.0 g, 0.00439 mol as PTC) was refluxed for more than 12 hours in a suitable reaction flask. The reacted solution may be used directly in the next step or cooled and filtered to obtain the target product in ee=0% (68 g, yield 94.6%).

Example 62

Synthesis of (±)-(2-chlorophenyl)-(4,5,6,7-4H-thieno [3,2,-c]pyrid-5-yl) sodium acetate (V)

The mixture of (S)-(2-chlorophenyl)-(4,5,6,7-4H-thieno [3,2,-c]pyrid-5-yl) acetonitrile (60 g, 0.236 mol), aqueous NaOH (40%, 360 g), methanol (100 mL), benzyltributylphosphonium chloride (0.5 g, 0.00152 mol) was refluxed for more than 15 hours in a suitable reaction flask. The reacted solution may be used directly in the next step or cooled and filtered to obtain the target product in ee=0% (63 g, yield 92%).

Example 63

Synthesis of (±)-(2-chlorophenyl)-(4,5,6,7-4H-thieno [3,2,-c]pyrid-5-yl) potassium acetate (V)

The mixture of (S)-(2-chlorophenyl)-(4,5,6,7-4H-thieno [3,2,-c]pyrid-5-yl) acetonitrile (64 g,), aqueous KOH (35%, 360 g), n-butanol (100 mL), TEBA (1.0 g, 0.00439 mol as PTC) was refluxed for more than 10 hours in a suitable reaction flask. After cooling and filtration, the target product was obtained in (64 g, yield 83.5%).

Example 64

Synthesis of (±)-(2-chlorophenyl)-(4,5,6,7-4H-thieno [3,2,-c]pyrid-5-yl) sodium acetate (V)

The mixture of (R)-(2-chlorophenyl)-(4,5,6,7-4H-thieno [3,2,-c]pyrid-5-yl) acetamide (60 g, 0.196 mol), aqueous NaOH (50%, 360 g), methanol (100 mL), TEBA (1.0 g, 0.00439 mol as PTC) was refluxed for more than 15 hours in a suitable reaction flask. After cooling and filtration, the target product was obtained in ee=0% (61 g, yield 94.6%).

Example 65

Synthesis of (±)-(2-chlorophenyl)-(4,5,6,7-4H-thieno [3,2,-c]pyrid-5-yl) sodium acetate (V)

The mixture of (R)-(2-chlorophenyl)-(4,5,6,7-4H-thieno [3,2,-c]pyrid-5-yl) acetamide (60 g, 0.196 mol), aqueous NaOH (35%, 360 g), n-butanol (100 mL), PEG400 (1.5 g, 0.00375 mol as PTC) was put into suitable reaction kettle under 4 atm pressure and refluxed for 12 hours. After cooling and filtration, the target product was obtained in ee=0% (60 g, yield 93%).

Example 66

Synthesis of (±)-(2-chlorophenyl)-(4,5,6,7-4H-thieno [3,2,-c]pyrid-5-yl) potassium acetate (V)

The mixture of (R)-(2-chlorophenyl)-(4,5,6,7-4H-thieno [3,2,-c]pyrid-5-yl) acetamide (60 g, 0.196 mol), aqueous KOH (40%, 360 g), ethanol (100 mL), 18-crown-6 (0.2 g, 0.00064 mol as PTC) was put into a suitable reaction kettle under 2 atm pressure and refluxed for 18 hours. After cooling and filtration, the target product was obtained in ee=0% (64 g, yield 94.5%).

Example 67

Synthesis of (±)-(2-chlorophenyl)-(4,5,6,7-4H-thieno [3,2,-c]pyrid-5-yl) potassium acetate (V)

The mixture of (R)-(2-chlorophenyl)-(4,5,6,7-4H-thieno [3,2,-c]pyrid-5-yl) acetamide (60 g, 0.187 mol), aqueous KOH (50%, 360 g), n-butanol (100 ml), PEG600 (1.5 g, 0.0025 mol as PTC) was put into a suitable reaction kettle under 2 atm pressure and refluxed for 15 hours. After cooling and filtration, the target product was obtained in ee=0% (65 g, yield 96%).

Example 68

Synthesis of (±)-(2-chlorophenyl)-(4,5,6,7-4H-thieno [3,2,-c]pyrid-5-yl) sodium acetate (V)

The same procedure as described for example 46, while (S)-(2-chlorophenyl)-(4,5,6,7-4H-thieno[3,2,-c]pyrid-5-yl) acetamide was used instead of (R)-(2-chlorophenyl)-(4,5,6, 7-4H-thieno[3,2,-c]pyrid-5-yl) acetamide, and the target product was obtained in ee=0% (61 g, yield 94.6%).

Example 69

Synthesis of (±)-(2-chlorophenyl)-(4,5,6,7-4H-thieno [3,2,-c]pyrid-5-yl) sodium acetate (V)

The same procedure as described for example 47, while (S)-(2-chlorophenyl)-(4,5,6,7-4H-thieno[3,2,-c]pyrid-5-yl) acetamide was used instead of (R)-(2-chlorophenyl)-(4,5,6, 7-4H-thieno[3,2,-c]pyrid-5-yl) acetamide, and the target product was obtained in ee=0% (62 g, yield 94.6%).

Example 70

Synthesis of (±)-(2-chlorophenyl)-(4,5,6,7-4H-thieno [3,2,-c]pyrid-5-yl) potassium acetate (V)

The same procedure as described for example 48, while (S)-(2-chlorophenyl)-(4,5,6,7-4H-thieno[3,2,-c]pyrid-5-yl) acetamide was used instead of (R)-(2-chlorophenyl)-(4,5,6, 7-4H-thieno[3,2,-c]pyrid-5-yl) acetamide, and the target product was obtained in ee=0% (65 g, yield 96%).

Example 71

Synthesis of (±)-(2-chlorophenyl)-(4,5,6,7-4H-thieno [3,2,-c]pyrid-5-yl) acetic acid (VI)

The mixture of (R)-(2-chlorophenyl)-(4,5,6,7-4H-thieno-[3,2,-c]pyrid-5-yl) acetic acid (61 g, 0.199 mol), aqueous NaOH (40%, 360 g) was refluxed for 18 h in a suitable reaction flask. The reaction solution was adjusted to pH 4-5 with acetic acid, and cooled with stirring to room temperature, After filtration and drying, (±)-(2-chlorophenyl)-(4,5,6, 7-4H-thieno[3,2,-c]pyrid-5-yl) acetic acid (VI) was obtained as white solid powder in ee=0% (60 g, yield 98.4%).

The obtained product was characterized with IR, MS and $^1$H NMR.

IR (cm$^{-1}$): 1650 (s, —C=O), 3400 (—OH).

MS (m/z): 308.1 (M+H)$^+$ $^1$H NMR (CDCl$_3$): δ 7.2-7.9 (4H, m), 7.1 (1H, d), 6.6 (1H, d), 3.57, 3.67 (2H, d), 4.1 (2H, s), 3.3-3.4 (2H, s).

The invention claimed is:

1. A method of preparing a compound of formula (I):

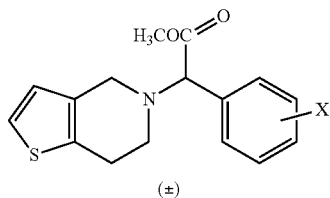

comprising preparing a compound of formula (V):

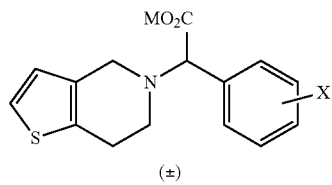

by direct alkaline hydrolysis of a compound of formula (IV):

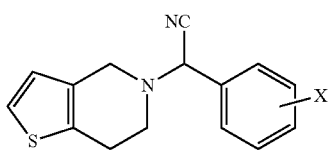

in a mixture of 20% to 50% aqueous base and a first organic solvent, in the presence of a first phase transfer catalyst (PTC) at an alkaline hydrolysis temperature of 60° C. to 130° C.; and reacting the compound of formula (V) with a methylation agent in an aqueous alkaline solution catalyzed by a second phase transfer catalyst (PTC) in $H_2O$ or a second organic solvent or a mixture thereof at an esterification temperature of 0° C. to 100° C., wherein X is selected from the group consisting of hydrogen, fluoro, chloro, bromo and iodo atoms and M is an alkali metal ion.

2. The method of claim 1, wherein the compound of formula (I) is clopidogrel, where X is 2–Cl.

3. The method of claim 1, wherein M is Na or K ion.

4. The method of claim 1, wherein the methylation agent comprises one or a combination of more than one selected from the group consisting of $Me_2SO_4$, $CH_3Cl$, $CH_3Br$, $CH_3I$ and $(CH_3O)_3PO_4$; the molar ratio of the methylation agent to the compound of formula (V) is 1:1 to 5:1; the second organic solvent comprises one or a combination of more than one selected from the group consisting of $CH_3OH$, ethanol or $C_1$-$C_8$ alcohols; ethyl acetate, butyl acetate; acetone, butanone, methyl isobutyl ketone; toluene, xylene, chlorobenzene, dichloromethane, chloroform; dichloroethane, DMF, DEF, DMSO, THF, DME, dioxane and acetonitrile; the aqueous alkaline solution comprises one or more bases selected from the group consisting of NaOH, KOH, $NaHCO_3$, $Na_2CO_3$, $KHCO_3$, $K_2CO_3$, $Et_3N$, pyridine, N,N-dialkylaniline and sodium alkoxylate; the pH of the aqueous alkaline solution is 8 to 12; the esterification temperature is 30° C. to 80° C.; the second PTC is selected from the group consisting of quaternary ammonium salt, quaternary phosphonium salt, PEG200-3000 and crown ethers; and the amount of the second PTC is 0.5% to 5% of the weight of the compound of formula (V).

5. The method of claim 4, wherein the molar ratio of the methylation agent to the compound of formula (V) is 1:1 to 3:1; the second organic solvent comprises one or a combination of more than one selected from the group consisting of methanol, n-butanol and toluene; the pH of the aqueous alkaline solution is 8 to 10; and the second PTC is selected from the group consisting of benzyltriethylammonium chloride, PEG400, PEG600 and PEG800.

6. The method of claim 1, wherein the first PTC comprises one or a combination of more than one selected from the group consisting of quaternary ammonium salt, quaternary phosphonium salt, PEG200-3000 and crown ethers; the amount of the first PTC is 0.5% to 5% of the weight of the compound of formula (IV); the first organic solvent comprises one or a combination of more than one selected from the group consisting of $C_1$-$C_8$ alcohols; the alkaline hydrolysis temperature is 90° C. to 120° C.; the aqueous base comprises at least one of sodium hydroxide and potassium hydroxide; the concentration of the aqueous base is 35% to 50%; and the molar ratio of the base to the compound of formula (IV) is 1:1 to 20:1.

7. The method of claim 6, wherein the first PTC is selected from the group consisting of benzyltriethylammonium chloride, PEG400, PEG600 and PEG800; the first organic solvent comprises one or a combination of more than one selected from the group consisting of methanol, ethanol and n-butanol; and the molar ratio of the base to the compound of formula (IV) is 15:1 to 20:1.

8. The method of claim 1, wherein the compound of formula (IV) is prepared by reacting a compound of formula (II):

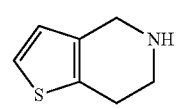

or a hydrochloride or sulfate salt thereof with a compound of formula (III):

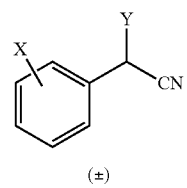

in a third organic solvent in the presence of a base at a reaction temperature of 0° C. to 110° C., wherein Y is Br, Cl or an ester group.

9. The method of claim 8, wherein X is 2–Cl.

10. The method of claim 8, wherein Y is Br or Cl.

11. The method of claim 8, wherein the ester group is selected from the group consisting of p-toluene sulfonyl, p-nitrobenzene sulfonyl, benzene sulfonyl, methyl sulfonyl and acetoxyl group; the third organic solvent comprises one or a combination of more than one selected from the group consisting of ethyl acetate, butyl acetate, acetone, butanone, methyl isobutyl ketone, toluene, xylene, chlorobenzene, dichloromethane, dichloroethane, chloroform, DMF, DEF, DMSO, THF, DME, dioxane, acetonitrile, methanol and n-butanol; the amount of the third organic solvent is 1 ml to 5 ml per gram of the compound of formula (III); the base comprises one or a combination of more than one selected from the group consisting of NaOH, KOH, NaHCO₃, Na₂CO₃, KHCO₃, K₂CO₃, Et₃N, pyridine, N,N-dialkylaniline and sodium alkoxylate; the molar ratio of the base to the compound of formula (III) is 1:1 to 5:1; and the reaction temperature is 50° C. to 80° C.

12. The method of claim 11, wherein the third organic solvent comprises methanol, n-butanol, or a combination thereof; and the base is NaHCO₃.

13. The method of claim 8, wherein the compound of formula (III) is prepared by halogenation of a compound of formula (VIII):

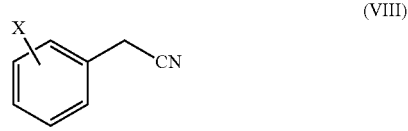

(VIII)

with a halogen at a halogenation temperature of 80° C. to 150° C., wherein Y is Br or Cl.

14. The method of claim 13, wherein X is 2–Cl.

15. The method of claim 13, wherein the halogen is bromine or chlorine; the halogenation temperature is 100° C. to 130° C.; and the molar ratio of the halogen to the compound of formula (VIII) is 0.5:1 to 1.5:1.

16. The method of claim 15, wherein the molar ratio of the halogen to the compound of formula (VIII) is 0.9:1 to 1.2:1.

17. The method of claim 8, wherein the compound of formula (III) is prepared by reacting a compound of formula (IX):

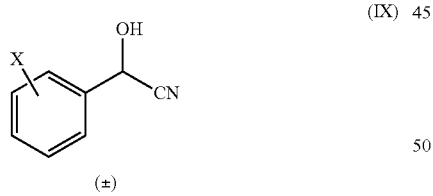

(IX)

with an esterification agent under an alkaline condition in an organic solvent at 0° C. to 100° C., wherein Y is the ester group, the esterification agent comprises one or a combination of more than one selected from the group consisting of sulfonyl chloride, acyl chloride, acid anhydride and organic acid.

18. The method of claim 17, wherein X is 2–Cl.

19. The method of claim 17, wherein the esterification agent comprises one or a combination of more than one selected from the group consisting of p-toluenesulfonylchloride, 4-nitrobenzenesulfonyl chloride, benzenesulfonyl chloride, methanesulfonyl chloride, acetyl chloride, acetic anhydride and acetic acid.

20. A method of preparing a compound of formula (I):

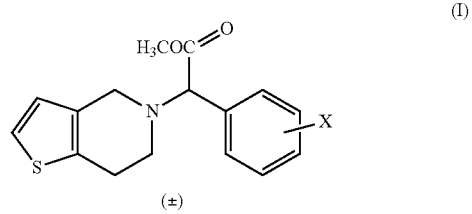

(I)

comprising preparing a compound of formula (V):

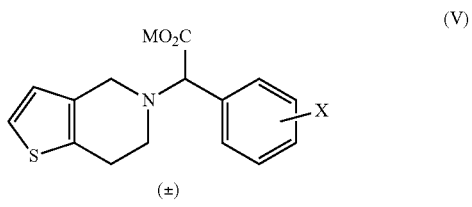

(V)

by direct alkaline hydrolysis of a compound of formula (VII):

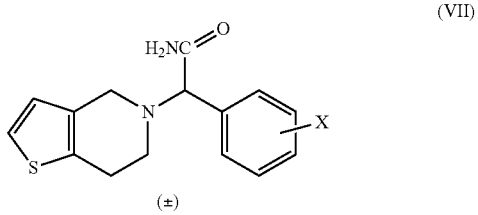

(VII)

in a mixture of 20% to 50% aqueous base and a first organic solvent, in the presence of a first phase transfer catalyst (PTC) at an alkaline hydrolysis temperature of 80° C. to 200° C. under a pressure of 1 atm to 11 atm, and reacting the compound of formula (V) with a methylation agent in an aqueous alkaline solution catalyzed by a second phase transfer catalyst (PTC) in H₂O or a second organic solvent or a mixture thereof at an esterification temperature of 0° C. to 100° C., wherein X is selected from the group consisting of hydrogen, fluoro, chloro, bromo and iodo atoms and M is an alkali metal ion.

21. The method of claim 20, wherein X is 2–Cl.

22. The method of claim 20, wherein the first PTC is selected from the group consisting of quaternary ammonium salt, quaternary phosphonium salt, PEG200-3000 and crown ethers; the amount of the first PTC is 0.1% to 10% by weight of the compound of formula (VII); the first organic solvent comprises one or a combination of more than one selected from the group consisting of C1-C8 alcohols; the aqueous base comprises sodium hydroxide, potassium hydroxide or a mixture thereof; the concentration of the aqueous base is 35% to 50%; the molar ratio of the base to the compound of formula (VII) is 1:1 to 20:1; and the alkaline hydrolysis temperature is 90° C. to 120° C.

23. The method of claim 22, wherein the first PTC is selected from the group consisting of benzyltriethylammonium chloride, PEG400, PEG600 and PEG800; the amount of the first PTC is 0.5% to 5% by weight of the compound of formula (VII); the first organic solvent comprises one or a combination of more than one selected from the group consisting of methanol, ethanol and n-butanol; the molar ratio of the base to the compound of formula (VII) is 15:1 to 20:1; and the pressure is 1 atm to 3 atm.

24. The method of claim 8, wherein the synthetic route for the preparation of the compound of formula (I), from the compound of formula (III) to the compound of formula (IV), to the compound of formula (V), and further to the compound of formula (I), is carried out in a "one-pot" process without strict separation or purification of every related intermediate.

25. The method of claim 24, wherein the synthetic route for the preparation of the compound of formula (V), from the compound of formula (III) to the compound of formula (IV), and further to compounds of formula (V), is carried out in a "one-pot" process without strict separation or purification at every step.

26. The method of claim 1, further comprising kinetic resolution of the racemic compound of formula (I) using a method comprising:
reacting the racemic compound of formula (I) with (R)-(−) camphor sulfonic acid in a resolution solvent at a resolution temperature of 90° C. to 120° C. to precipitate out (S)-compound of formula (I) camphor sulfonate;
neutralizing the (S)-compound of formula (I) camphor sulfonate with a neutralization base in an organic solvent to obtain (S)-compound of formula (I) free base soluble in the organic solvent and camphor sulfonate insoluble in the organic solvent; and
separating the (S)-compound of formula (I) free base from the camphor sulfonate.

27. The method of claim 26, further comprising racemization of enantiomers using a method comprising hydrolyzing and racemizing the (R) isomer of a compound of formula (XIII)

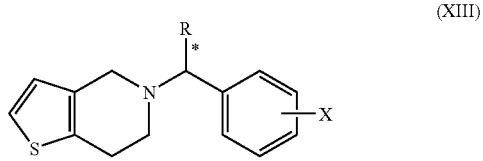

(XIII)

wherein R is —COOH, —CONH$_2$, —CO$_2$CH$_3$ or —CN, in a mixture of 10% to 50% aqueous base and an organic solvent, in the presence of a phase transfer catalyst (PTC) at 80° C. to 200° C., under a pressure of 1 atm to 11 atm to obtain a racemic compound of formula (V); and
re-using the racemic compound of formula (V) in the method of preparing the compound of formula (I).

28. The method of claim 27, wherein X is 2–Cl and the (S)-compound of formula (I) is S-(+)-clopiodogrel.

29. The method of claim 20, wherein M is Na or K ion.

30. The method of claim 20, wherein the methylation agent comprises one or a combination of more than one selected from the group consisting of Me$_2$SO$_4$, CH$_3$Cl, CH$_3$Br, CH$_3$I and (CH$_3$O)$_3$PO$_4$; the molar ratio of the methylation agent to the compound of formula (V) is 1:1 to 5:1; the second organic solvent comprises one or a combination of more than one selected from the group consisting of CH$_3$OH, ethanol or C$_1$-C$_8$ alcohols; ethyl acetate, butyl acetate; acetone, butanone, methyl isobutyl ketone; toluene, xylene, chlorobenzene, dichloromethane, chloroform; dichloroethane, DMF, DEF, DMSO, THF, DME, dioxane and acetonitrile; the aqueous alkaline solution comprises one or more bases selected from the group consisting of NaOH, KOH, NaHCO$_3$, Na$_2$CO$_3$, KHCO$_3$, K$_2$CO$_3$, Et$_3$N, pyridine, N,N-dialkylaniline and sodium alkoxylate; the pH of the aqueous alkaline solution is 8 to 12; the esterification temperature is 30° C. to 80° C.; the second PTC is selected from the group consisting of quaternary ammonium salt, quaternary phosphonium salt, PEG200-3000 and crown ethers; and the amount of the second PTC is 0.5% to 5% of the weight of the compound of formula (V).

31. The method of claim 30, wherein the molar ratio of the methylation agent to the compound of formula (V) is 1:1 to 3:1; the second organic solvent comprises one or a combination of more than one selected from the group consisting of methanol, n-butanol and toluene; the pH of the aqueous alkaline solution is 8 to 10; and the second PTC is selected from the group consisting of benzyltriethylammonium chloride, PEG400, PEG600 and PEG800.

32. The method of claim 20, further comprising kinetic resolution of the racemic compound of formula (I) using a method comprising:
reacting the racemic compound of formula (I) with (R)-(−) camphor sulfonic acid in a resolution solvent at a resolution temperature of 90° C. to 120° C. to precipitate out (S)-compound of formula (I) camphor sulfonate;
neutralizing the (S)-compound of formula (I) camphor sulfonate with a neutralization base in an organic solvent to obtain (S)-compound of formula (I) free base soluble in the organic solvent and camphor sulfonate insoluble in the organic solvent; and
separating the (S)-compound of formula (I) free base from the camphor sulfonate.

33. The method of claim 32, further comprising racemization of enantiomers using a method comprising hydrolyzing and racemizing the (R) isomer of a compound of formula (XIII)

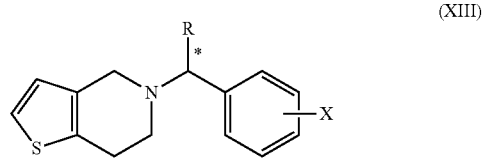

(XIII)

wherein R is —COOH, —CONH$_2$, —CO$_2$CH$_3$ or —CN, in a mixture of 10% to 50% aqueous base and an organic solvent, in the presence of a phase transfer catalyst (PTC) at 80° C. to 200° C., under a pressure of 1 atm to 11 atm to obtain a racemic compound of formula (V); and
re-using the racemic compound of formula (V) in the method of preparing the compound of formula (I).

34. The method of claim 33, wherein X is 2–Cl and the (S)-compound of formula (I) is S-(+)-clopiodogrel.

* * * * *